US007122311B2

(12) United States Patent
Whittaker et al.

(10) Patent No.: US 7,122,311 B2
(45) Date of Patent: Oct. 17, 2006

(54) METHODS FOR DETERMINING THE RISK OF DEVELOPING ASTHMA CHARACTERIZED BY BRONCHIAL HYPERRESPONSIVENESS

(75) Inventors: Paul Andrew Whittaker, Horsham West Sussex (GB); Deborah Alexis Meyers, Mocksville, NC (US); Dirkje Sjoukje Postma, Groningen (NL); Eugene Roland Bleecker, Bermuda Run, NC (US)

(73) Assignees: Novartis AG, Basel (CH); Wake Forest University Health Sciences, Winston-Salem, NC (US); Rijksuniversiteit Groningen, Groningen (NL)

( * ) Notice: Subject to any disclaimer, the term of this patent is extended or adjusted under 35 U.S.C. 154(b) by 434 days.

(21) Appl. No.: 10/194,370

(22) Filed: Jul. 12, 2002

(65) Prior Publication Data

US 2003/0096270 A1   May 22, 2003

Related U.S. Application Data

(60) Provisional application No. 60/305,649, filed on Jul. 16, 2001.

(51) Int. Cl.
*C12Q 1/68* (2006.01)
*C07H 21/02* (2006.01)
*C07H 21/04* (2006.01)

(52) U.S. Cl. .................. 435/6; 536/23.5; 536/24.31

(58) Field of Classification Search .................. 435/6, 435/91.2, 7.1, 4; 536/23.1, 23.5, 24.31, 24.33
See application file for complete search history.

(56) References Cited

U.S. PATENT DOCUMENTS 5,643,781 A    7/1997   Suzuki

FOREIGN PATENT DOCUMENTS

WO    96/00289   1/1996

OTHER PUBLICATIONS

Whittaker, P.A. Current Opinion in Pharmacology. 2003. 3:212-219.*
Lucentini, J. The Scientist. Dec. 2004, p. 20.*
Sano et al, The EMBO Journal, vol. 12, No. 6, "Protocadherins; a large family of cadherin-related molecules in central nervous system", pp. 2249-2256 (1993).
Meyers et al, Genomics, vol. 23, "Evidence for a Locus Regulating Total Serum IgE Levels Mapping to Chronosome 5", pp. 464-470 (1994).
Bleecker et al, Clinical and Experimental Allergy, vol. 25, Supplement 2, "Evidence for linkage of total serum IgE and bronchial hyperresponsiveness to chromosome 5q: a major regulatory locus important in asthma", pp. 84-88 (1995).
Sano et al, The EMBO Journal, vol. 12, No. 6, "Protocadherins; a large family of cadherin-related molecules in central nervous system", pp. 2249-2256 (1993).
Takeichi, Annu. Rev. Biochem., vol. 59, "Cadherins: A molecular family important in selective cell—cell adhesion", pp. 237-252 (1990).
Meyers et al, Genomics, vol. 23, "Evidence for a Locus Regulating Total Serum IgE Levels Mapping to Chronosome 5", pp. 464-470 (1994).
Postma et al, New England Journal of Medicine, vol. 333, "Genetic Susceptibility to Asthma—Bronchial Hyperresponsiveness coinherited with a major gene for atopy", pp. 894-900 (1995).
Bleecker et al, Clinical and Experimental Allergy, vol. 25, Supplement 2, "Evidence for linkage of total serum IgE and bronchial hyperresponsiveness to chromosome 5q: a major regulatory locus important in asthma", pp. 84-88 (1995).

* cited by examiner

*Primary Examiner*—Carla J. Myers
(74) *Attorney, Agent, or Firm*—Gregory C. Houghton

(57) ABSTRACT

The invention relates to the use of an asthma-associated gene, designated AAGA, the protein molecule encoded by AAGA and related molecules in diagnostic and prognostic screening of patient populations, to polymorphisms in AAGA, and to the use of the protein encoded by AAGA or a variant thereof as a therapeutic target.

4 Claims, No Drawings

SEQUENCE LISTING

<160> NUMBER OF SEQ ID NOS: 94

<210> SEQ ID NO 1
<211> LENGTH: 19761
<212> TYPE: DNA
<213> ORGANISM: Homo sapiens

<400> SEQUENCE: 1

```
aaggacaggc cagggcagct cccaatgcca attccagggc tagtcagccc tgaccacagt      60
tctgacccca atcttgacct gtgttccctt gtacgcacct gcccatggca gcaggaggga     120
gaggagagga gccctagcaa ctgtgcatgt tcctgtgtgc atgctctggg gcatgtgtgc     180
atgctctggg gcatgtgtgc acgctctgtg gcctgtgtgc acgttctggg gcatatgtgt     240
tgggggaaag tcgggaaggc taacacctac tcctcaaccc taaccatttt cacaagcctt     300
gcccaattca agctggcctt ttatgggggt ggagaatact gggcaccgtg ggtgattgtc     360
agaaaaagag gatttgagat gtcatacctc atgcatatgc actgacttgg catctcagaa     420
caaagagaaa tgagacatca tccctctcc ctccagccaa ccttaatgga gcccagtgtg      480
acaagtcaag gtcccagggt ctggggtgtg taaggacgta cttgtgtctc tttcctacca     540
tgcatgtggg gagggtgct ccagttgggg atgctcgagg tctcacccgt ccactggctc     600
tctctcccta tctcagtatc aaggtaatta ccatcggtga ctaaggcagg atgctcgtga     660 gaaggagtg ttgggtgaag cacagagcag agagcaagga ggaaaagaag gaaagagggc     720
gggcagccgg gcttgggccc agggagcgtc aggtgggtga gggtgttcca tgggcgggag     780
ctgctctagg catgccaggc ctcttactgg ctcctccagc tggggcagac actgctgcta     840
cacccagctg tggatgagat tcagggatct gagtttctgg aatcggggtt ctgtgctggg     900
actgactgct cttgtggaga atcgtgtgtc agtgggagag ggtgagtatg gggccagctc     960
tgggcagctc agggccaggc ttttcttccc agctcatggc ctctgttttg cctcttcccc    1020
ttgcagcctt cctgattctg gggcctccca ggatggagcc cctgaggcac agcccaggcc    1080 ctgggggca acggctactg ctgccctcca tgctgctagc actgctgctc ctgctggctc    1140
```

-continued

```
catccccagg ccacgccact cgggtagtgt acaaggtgcc ggaggaacag ccacccaaca      1200
ccctcattgg gagcctcgca gccgactatg gttttccaga tgtggggcac ctgtacaagc      1260
tagaggtggg tgccccgtac cttcgcgtgg atggcaagac aggtgacatt ttcaccaccg      1320
agacctccat cgaccgtgag gggctccgtg aatgccagaa ccagctccct ggtgatccct      1380
gcatcctgga gtttgaggta tctatcacag acctcgtgca gaatggcagc ccccggctgc      1440
tagagggcca gatagaagta caagacatca atgacaacac acccaacttc gcctcaccag      1500
tcatcactct ggccatccct gagaacacca catcggctc actcttcccc atcccgctgg      1560
cttcagaccg tgatgctggt cccaacgtgt ggcatccta tgagctgcag gctgggcctg      1620
aggcccagga gctatttggg ctgcaggtgg cagaggacca ggaggagaag caaccacagc      1680
tcattgtgat gggcaacctg accgtgagc gctgggactc ctatgacctc accatcaagg      1740
tgcaggatgg cggcagcccc ccacgcgcca gcagtgccct gctgcgtgtc accgtgcttg      1800
acaccaatga caacgccccc aagtttgagc ggccctccta tgaggccgaa ctatctgaga      1860
atagccccat aggccactcg gtcatccagg tgagaggccc cctccgtata actgtcaggg      1920
tgacccacca ctagaaatgg gagcccaccc aaccaggtga gagttccctt cacttagggg      1980
aaaaactgcc agaatactgt agtgagaccc cttctcccca aactcagcca ggggagtctt      2040
tcccacccca ccccagcagg tgatattact ttcctctatc aggctactta ggtgacagtg      2100
aaatagcata tgaacagttt cccgtgaccc ctaaggcaga ctcaagctgg gggaacctct      2160
gagaagtaaa actcccgccc tagtcaagta gatccttctc tgctagccag gtgagctgag      2220
ttggaacaaa ggaatcaccg tttatccagg tagaatctct cctgagatga gagtatcttc      2280
ccaaccaggg atagtttctc tttagccaga tgaggttttc ctgaagctgg aggatatagc      2340
ctcattttgc ctcttcctga caaagtcaga tgagatcatt ttagccaggt gggaccctca      2400
gagttctgaa aaacatact aggggtgtctg tatacatgcc tcctccccta ggcatggggt      2460
gcccatagat gtggggtgct tggtacagtg gggttcagtg gggggtcaat ttcctctgtt      2520
gaagttctca gcacccctct ccatgggaac tgcccaggc actaggcagc ttggtggggc      2580
tggggactgg gagggagcaa agaaagcgtc tctgcagaca ggtgggtgta tctcccgctg      2640
tcatctcagc tctggcctcc tgccagcccc agctcctttc cccttcccca tgggctgaag      2700
atgcctctct ctttgatgtg agggagctga ggaggctcgg cctgccctgg acaccattac      2760
ccatcctgga aaaccttag tcctgggtcc tcaagccaaa gtgggagatg ggtgggagtt      2820
tcagcctttt ttttttttt tagagcctgg tggactggga cctggaaaag agactgagaa      2880
agaaaaggga gacagacagt cggggatagc aaataataat agcctaggtg ccaggcaccg      2940
ttctaaacac atgatgtgta ttatatcatt taatccttac agtacaaggt aagtattatc      3000
cccattttgc agatgagaaa ccgggcccaa acagattaga aaactcgcct gatatcctac      3060
agctaatgag ttcagagtcc acctttgccg cagccaagag tctggcttca gagcctaggt      3120
gtgtaagagc tttaccacct cccagtgagg tgaagcggga gagtagggca gagagtaagc      3180
agagaggtca gcaggctga aaagagagca tggaagaaaa caggctgtgg gaaaggggaa      3240
gaatcagaac tgagcaagga tagaaaggag acagaagcca agagtcacag agacaaagag      3300
aggtaagaca agagacagat aagctggaag accaatctag agccaaggga gactgggat      3360 cctcatcata aagttgatga caggtagact ggggtgaggg gaggagaaac tgttagggtt      3420
tggcactcag agatgtgagc agagaccagg gtacctgggg aaccattgcc caggagtctt      3480
cactgtagga aaagcccagg cggggatagc tggagttccc attcccaagg aggagaggac      3540
```

-continued

```
tggcagtggc ttgagggctc actaggtgca gtgcccacta ctgcattagc actgatttt     3600
cagaggcagg cgggtaggag ggtagatggt tggacagaca aaaagaaata catgctcttt    3660
agggagcact ttccctgtgc cgggcaatgt caggcatttt tacctgtatt atcccatttg    3720
atgctcacca cagttctgtg aaataggtta cattattatc cccatttcac acattcatag   3780
actgaggctt agggaggtta ataattggc ccaaggtcac atagttactt gggaagtggt    3840
ataactggga tttgaaccca ggactcttct gttttgttac cccagagact ctgccaagtt   3900
atgcttattc tccctcact ccccacagca gtcacattct gtctggctgt gacctaactc    3960
cagccctcat gtttctccct gcccagtagt accccatggc cattcccacc tgggtcctct   4020
tccccattac caaccatgtt tgtatagagt tgagtcgagt gcgcgttgga gttggcgtgg   4080
gagggtgtgc ccgctgactg cagagggaca gacagttcat tgtttgatgc tgggagccca   4140
gcccactgcc agcaggctct gtggcctgca tcaacccctc cctcctggct gcaggctcag   4200
gccggattcc tcgcattggt gcctcgccag ccggtgccag tcgggaggag aagttgctgc   4260
tgaaacaggt ttccccggtt tgacagagcg gtggctgggg cccggcctgg agggcttctc   4320
tgacccacaa ccctacctga cttctttcaa aagaaatccc ccaacctggg gccttcagat    4380
gggcatgtga gtcttactc atgtgtgcaa acacacatat gcacaaacac atataccttc   4440
tcacacaaaa atcacacata atcacacatt ctgacacaat catacacata caaacacata   4500
taccttctca cacaaacata tcacatttaa tcacacattc tgacacaatc atacacatac   4560
atatgtgcat gcgtgcgtgc atgtagtgca cattcacacg ggcacacaca ccgcctctac   4620
tactcgcacc tctccatctc ttcaggaggg ttcaggcagg gttcattggt gaaatggctt   4680
ccctagttct attggatcct catcctctcc tggtatttt gtggacccat acagcaatga   4740
caagtgaggt ttaattctgc cctgtcccat ctccaatagt tgcctgtagc actgttgagg   4800
atttgcaggc tgcatctggg ctcttcagga aaataggtta gtaatgcctg ccagaatgtc   4860
cgaattggga aaaggcagga cacacatggc ttctggaaag ggagcgatgt tggattggct   4920
gtgtctgcca tgcttgttgg aaaggacatt ggcagcatgt gtgccccttt atttgctatc   4980
cctgatctaa accatctctg ttctccttgt ttttctctcc tgcccataag gtgaaggcca   5040
atgactcaga ccaaggtgcc aatgcagaaa tcgaatacac attccaccag gcgcccgaag   5100
ttgtgaggcg tcttcttcga ctggacagga acactggact tatcactgtt cagggcccgg   5160
tggaccgtga ggacctaagc accctgcgct tctcagtgct tgctaaggac cgaggcacca   5220
acccccaagag tgcccgtgcc caggtggttg tgaccgtgaa ggacatgaat gacaatgccc   5280
ccaccattga gatccgggc atagggctag tgactcatca agatgggatg ctaacatct    5340
cagaggatgt ggcagaggag acagctgtgg ccctggtgca ggtgtctgac cgagatgagg   5400
gagagaatgc agctgtcacc tgtgtggtgg caggtgatgt gcccttccag ctgcgccagg   5460
ccagtgagac aggcagtgac agcaagaaga agtatttcct gcagactacc accccgctag   5520
actacgagaa ggtcaaagac tacaccattg agattgtggc tgtggactct ggcaaccccc   5580
cactctccag cactaactcc ctcaaggtgc aggtggtgga cgtcaatgac aacgcacctg   5640
tcttcactca gagtgtcact gaggtcgcct tcccggaaaa caacaagcct ggtgaagtga   5700
ttgctgagat cactgccagt gatgctgact ctggctctaa tgctgagctg gtttactctc   5760
tggagcctga gccggctgct aagggcctct tcaccatctc acccgagact ggagagatcc   5820
aggtgaagac atctctggat cgggaacagc gggagagcta tgagttgaag gtggtggcag   5880
ctgaccgggg cagtcctagc ctccagggca cagccactgt ccttgtcaat gtgctggact   5940
```

-continued

| | | | | |
|---|---|---|---|---|
| gcaatgacaa | tgaccccaaa | tttatgctga | gtggctacaa | cttctcagtg | atggagaaca | 6000 |
| tgccagcact | gagtccagtg | ggcatggtga | ctgtcattga | tggagacaag | ggggagaatg | 6060 |
| cccaggtgca | gctctcagtg | gagcaggaca | acggtgactt | tgttatccag | aatggcacag | 6120 |
| gcaccatcct | atccagcctg | agctttgatc | gagagcaaca | aagcacctac | accttccagc | 6180 |
| tgaaggcagt | ggatggtggc | gtcccacctc | gctcagctta | cgttggtgtc | accatcaatg | 6240 |
| tgctggacga | gaatgacaac | gcaccctata | tcactgcccc | ttctaacacc | tctcacaagc | 6300 |
| tgctgacccc | ccagacacgt | cttggtgaga | cggtcagcca | ggtggcagcc | gaggactttg | 6360 |
| actctggtgt | caatgccgag | ctgatctaca | gcattgcagg | tggcaaccct | tatggactct | 6420 |
| tccagattgg | gtcacattca | ggtgccatca | ccctggagaa | ggagattgag | cggcgccacc | 6480 |
| atgggctaca | ccgcctggtg | gtgaaggtca | gtgaccgcgg | caagccccca | cgctatggca | 6540 |
| cagccttggt | ccatctttat | gtcaatgaga | ctctggccaa | ccgcacgctg | ctggagaccc | 6600 |
| tcctgggcca | cagcctggac | acgccgctgg | atattgacat | tgctggggat | ccagaatatg | 6660 |
| agcgctccaa | gcagcgtggc | aacattctct | ttggtgtggt | ggctggtgtg | gtggccgtgg | 6720 |
| ccttgctcat | cgcctggcg | gttcttgtgc | gctactgcag | acagcgggag | gccaaaagtg | 6780 |
| gttaccaggc | tggtaagaag | gagaccaagg | acctgtatgc | ccccaagccc | agtggcaagg | 6840 |
| cctccaaggg | aaacaaaagc | aaaggcaaga | gagcaagtc | cccaaagccc | gtgaagccag | 6900 |
| tggaggacga | ggatgaggcc | gggctgcaga | agtccctcaa | gttcaacctg | atgagcgatg | 6960 |
| cccctgggga | cagtccccgc | atccacctgc | ccctcaacta | cccaccaggc | agccctgacc | 7020 |
| tgggccgcca | ctatcgctct | aactcccac | tgccttccat | ccagctgcag | ccccagtcac | 7080 |
| cctcagcctc | caagaagcac | caggtggtac | aggacctgcc | acctgcaaac | acattcgtgg | 7140 |
| gcaccgggga | caccacgtcc | acgggctctg | agcagtactc | cgactacagc | taccgcacca | 7200 |
| accccccaa | atacccagc | aagcaggtag | gccagccctt | tcagctcagc | acccccagc | 7260 |
| ccctacccca | cccctaccac | ggagccatct | ggaccgaggt | gtgggagtga | tggagcaggt | 7320 |
| ttactgtgcc | tgcccgtgtt | gggggccagc | ctgagccagc | agtgggaggt | ggggccttag | 7380 |
| tgcctcaccg | ggcacacgga | ttaggctgag | tgaagattaa | gggagggtgt | gctctgtggt | 7440 |
| ctcctccctg | ccctctcccc | actggggaga | gacctgtgat | ttgccaagtc | cctggaccct | 7500 |
| ggaccagcta | ctgggcctta | tgggttgggg | gtggtaggca | ggtgagcgta | agtggggagg | 7560 |
| gaaatgggta | agaagtctac | tccaaaccta | ggtctctatg | tcagaccaga | cctaggtgct | 7620 |
| tctctaggag | ggaaacaggg | agacctgggg | tcctgtggat | aactgagtgg | ggagtctgcc | 7680 |
| aggggagggc | accttcccat | tgtgccttct | gtgtgtattg | tgcattaacc | tcttcctcac | 7740 |
| cactaggctt | ctggggctgg | gtcccacatg | cccttgaccc | tgacaataaa | gttctctatt | 7800 |
| tttggagttt | tggtttctta | ttttctggaa | ctgagagaag | cagcgagaga | gactggaagc | 7860 |
| agcccttgt | cctcaggtcc | tacctcaatt | tccccttccc | ttctctttgc | ctcttgccac | 7920 |
| atcctagacc | tgcccattgt | accccacact | atcttagcct | accatcttgc | catccacccc | 7980 |
| catgtcccta | tccacgtctg | ggaaagtggc | cttctgacca | gccttcaaat | ggaggtgtct | 8040 |
| ggcaatgtgt | cccccttgccc | catgtctata | gggctttctt | cctaagaatg | acccagaaag | 8100 |
| ggcaggtgga | gctataccca | agtcctgccc | catctgagcc | ttgattttc | caatctgctc | 8160 |
| aaacagttgc | ctctgacaga | cctcagactg | gagcacctgg | tagggagtag | cattcagcct | 8220 |
| tccttcctgc | cttaggtgaa | ggcagagaac | ctcttgatta | caccagccac | cttccccag | 8280 |
| ggcaagtcct | tccctcaagt | cccttcccca | gcctcttcat | cccaacaaca | ggcaacaccc | 8340 |

```
agcaattcgc tggccctccc ctgtgtctcc ccaccatgat caccagcctg agctgcaggg   8400
agcggggccc tgggggagac atggcgaatt cctaagttct ttgcattgac ctgccctgca   8460
cccccactct tagggggttc cctgctcatg agcagaggct tcctagttct gccttccgcc   8520
tgtgatgcta cctccctccc cactttccac tccttgctct ggccaccctg ggttgcttgc   8580
ttgcactctc tctctctcca tctctcactt cttgctctcc tgggtctgcc ctgtctctgg   8640
ttgtgcctga gttggaggaa ggctaaatcg tggctgaggg gcctcaggcc ctggggagt    8700 ctctgaggcc agaggcaacc tatctccatg gtgactaaag aggcttgaga cactcccaag   8760
aggaccaagg ctccagctct ctcctctgat tccatccaca aattccccca atgccctggg   8820 ggcccccaa agtaaaaact ccttgggtcc ttggaggagt ggggcctggg gaagtgagat    8880
ctaaccatat cgtgatctcc agcaactcct gacctcccat tctttctctt cctttctgt    8940 cctttctggc attccttccg tctttctcct attcctttag cgtcttcatc tcttttcctt   9000
tcccatgatc tgagggattg tctcttactc agctctaatc caacctaacc catccatgga   9060
gccacactga atgtcttctc ccaacattca gatacaacca aaccacacca cctgttgtca   9120
tcatcaacac acacaggcca agtttccact gagtactcag catggtacta gaccctgatg   9180
aaaaaatggc catacttgta caagacagac aagtgaacga tgaggcaatt gagtgtcttg   9240
agtcgaatga gaagtgccct actaaagctt ttcccaactt attccatgaa actacttcta   9300
ctgctactgc tcacttcctt tttttttttt tttttttttt tgagatggag ttttgctctt   9360
gttgcccagg ctggagtgca atggcacgat ctcagctcac tgcaacctct gcctcccagg   9420
ttcaagcaat tctcctgcct cagcctcctg agtagctggg attacaggca tgtgccacca   9480
cacccagcta attttgtatt tttagtagag acagggtttc tccatgttgg tcaggctggt   9540
cttgagctcc tgacctcagg cgatctgccc gccgtggcct cccaaagtgc tgggattaca   9600
ggcatgagcc accatgcccg gcactcactt ccatttttg agtccttact aggtgtgagg    9660
taccatgcta agcactttgt gtgaattagt tcaatcagtg ctcataactc tttatgatat   9720
gggtcatttt aatattaatt ttgcagaagt gaaaactaaa tagtgatgca gccaaattca   9780
aacacaaagc aggcgggtct cctattacct attatgctat aaaaaaggcg ttctgtggtg   9840
aagttagttt tggtagtaag aaattcatga tcacattagc ctattaaagg ctctgcagag   9900
tcctccaaaa aaggggaac ctgttagact tcgtttaacc tttttttttt tttttttttg    9960
agacagggtc ttgctctgtc acccaggctg gagtgcaggg gcgcaatctt ggctcattgc  10020
aacctctgcc acctgggctc aagcgatcct cctgtgtagc tgggactaca gtcgtgcacc  10080
accacacctg gctaattttt gtaatttctg tagagacagg gttttgccat gttgcccagg  10140
ctggtctcaa ctcctgggct caagcgatct gcccacctca gcctcccaaa gtgcttggat  10200
gacaggtgtg agctgccgtg cctggcccca attttgttta cctcttgagt tttctgaatt  10260
tatttcacca tattgcccct cccttccttt gacgagcaca gtatgggaaa acttgtacaa  10320
gacatggaaa tgggcttctg gaaggagaaa gtcagcttgt caatgatgag caggattagg  10380
gcaggagggt cccctgcctc ctcacagggt caccgtgtaa gcaaactcct gcggcagaag  10440
tgaaccaagt tggaggcagg gaaagggcag aaaaaggaat attctggcaa gaagagggc   10500 ataagagaaa gctgaaagat gagactgaaa gaactgtagg ttgtagagga cataggtgcc  10560
ttaccaaaag ttcttcagaa ggaactagtc cctgaaagct catgagtgtt ttagatgaac  10620
tgagttttag aaagagcact ggaatatatg gtgggcttaa aagggcatag agatgaaggt  10680
acaggactga acctctaaga gttggactat gatggtggca atggggtgta tggatggatg  10740
```

```
gatttggcaa aggttaggga gaaaggaccc acaggattca agggataatt ggatatgagg      10800
tagggatagg gaatgagggg agagctacca ggattctcag gtagacatca gccttctgag      10860
tctgggtgat aggatagtga tgagatcatt gcccatacag aagctaattg aagaagcatt      10920
tggtttcaga catgttgaat cttaagggcc agtaggcaga gccaactgga ataatcagc       10980
aagtgtctag agcttcagga ctcaaagagt ttgagagaga ttttttgatc tgggctttta     11040
taatttgata gtcataaaat tagagggaac attaagtgtt gggtataacc caaccctcca     11100
ttttatggaa aagaatcatg ggaaaagaga ccaagcgact tgcttagtag gcaggaccaa     11160
agccttcaat taccagatat gggttctgca gggaggtggg actgctggcc agtatcttga     11220
aagaaaactg gaaagagaag caccaacaac catgttgccc tgtgcctccc agacccctcc     11280
tggaccctaa tcacccctac accagtggac tacactcct ttatagcctc ccggccccaa      11340
acatccatgt tagttttggg gaccttatca gtcatcaccc agacccttca gtgttttaga     11400
tcaatacaag gattccaaga acgtcgcttt attcctgaag atgaggtggg agccatcttc     11460
aggaatgggg atagtgggga ggcagttctg ggctaccttc acagcagctc caaaactcct    11520
gtcctgacag cctcttccac cctagctgcc ttgaatgggg ctattaggag ggtaagtcta    11580
caaagccagg gccacctccc ctggccatct tcataacctc ctatccagag ttatagagta   11640
agacaaagca ctgccaaagt cttggaggat gggaaggagc ttagagactc atcagcaggg   11700
ccctgggctt agctgttttc accctggcc tccagggacc ctgagtctgc accctccaca    11760
actcctaatt tctggttggc aggaaaatct gtggcagtcc caagtgggta tttgggtggc   11820
tggctggttg tgccaagtgc caagttgaga ttgccaggtt ccagggctga tcgttaacct   11880
gtggcaggca tacagggctg ctggctggga gcagcctgtc acggttccac tccccgacc    11940
cccagtcccc agtccaagcc tccaagtctg gctcctcatg ccagcagccc tcccagaagc   12000
tccttcctat ttcctggaag gagtctccct ttgagaccag cttccctaat ccctaatggg   12060
tgccatgccc tctccccatg tccaggctcc tggcagagcc ctaccctctc cagtgaatat   12120
tctatttcct gatcgggagg actgggggagt ttccattgtt ctgctttgtc cccttccccc  12180
aggtgccctg gtttgttatc aggctcctcc cttttttttcc actcccaggc ctctctggag  12240
gggagtgaag tggggatggg gggctgagtg ggaggggcga cagcagggag tcttcagact   12300
gctgcaacat cacaaaccag ggatgaggaa cacaggataa gaaaagaaag gttgttccct   12360
catttggaag gaggcagtgg caagagcagt gagacaggtg aggagctgga gtttggaggg   12420
tgctgtttgg aaatgaggga actaactgtt gtggtattgg tgagctgttt gggagttagg   12480
agtctgcttc ttttaggaag ctgttctaga aactgcaggc tatgctggtg tttagaggct   12540
gagctggaat tagggagtc gggtggtatt atgttactct ggtattgggc tctacaccgt    12600
attacaggtc attctgggat taaagggagg ctgtgccaat attgggaagc tgggttagaa    12660
ctagaagggt tgtgctataa caagcggttg cactggatga gggttattgg ggtagcatag    12720
gggctataat aacactgggg cctgcgctgt attgggactt ccagtatgtg gacttggctg    12780
tactaggagc ggtcctagaa ctcaggagct gtctttcact ggggcctgtg ctttcgggag   12840
gaatgtgctg tgctggggcc tgggtctctt cttggttgct gttgaagcct gagtaggatg    12900
gtgcttggct tgtactaggg cctggtatgg tggtgggccc tgtgggcaag ctggctggtc    12960
agtagtgaca atctgtctcc ctgcagttac ctcaccgccg cgtcaccttc tcggccacca   13020
gccaggccca ggagctgcag gacccatccc agcacagtta ctatgacagt ggcctggagg   13080
agtctgagac gccgtccagc aagtcatcct cagggcctcg actcggtccc ctggccctgc   13140
```

-continued

```
ctgaggatca ctatgagcgc accacccctg atggcagcat aggagagatg gagcaccccg    13200
agaatggtga ggcgcagcac catggtcagg gcacccagg aatgagtgga agcctgggaa     13260
tggtgacaag gccttaaaca aatcatctat gtattgagtt attatgtgct cagtcatcat    13320
caccgtgctg agggctttca ggtatacacg catttaatcc ccagaaccac tctgtgattt    13380
gagaacttta tggcacccac tttacagtgg aggaaactga ggcttagaga ggttaagtca    13440
cttgcccaaa gtcatacatc tagaacgtga cagacctggg agggattcaa acccaggttt    13500
ctctgactcc aaagctgttg cattcggcac catgtttaca cggccacctg ggaacaggga    13560
ccctgagtgt ggtggccaga aagctcacgt aatggtgagg aaaccttgag aaggtgggtg    13620
gtggtcctct aaggttggga aggccttgag aatagagatt gggccctgga tgctacaggg    13680
ggctcagaga atggagtgac gatatgctgg ggtgaggagt gggagaaggt ttggcacctc    13740
tttgaggaag agcgcggtag gaggtctggt gaagagaaag gcctgtctgg gagggatttg    13800
gagggtgatg gcaaaaagga ggtgtgagcc agcgcagagg tcggcatggg aatggatggt    13860
gaggtgtgcc gtcagtgtgt gtgcagtgcg tgtgcatgtg tgaagtcgtc catggcagcc    13920
tgtggagggg gagagtgaac gagctaaccc ctgagatgga aagactctct aagttggagt    13980
tgtcctcggg tcccacccac tccctcaact caaagcctcc tcgctccaca aaagatggga    14040
ggtttcactc ccctgcctca ggcacagggc ccttgtctaa cctcccaggc cctaggtctc    14100
agagtgccct ccaccccac cccgcccctc catgcgcgat ctcatgcccg tctcatcctt     14160
tttgtgcccg cgcagagccg gctggccgga gcaggccctg aggcagagtg ccaggtatgt    14220
gggaactgct ctggggtctg gggtctgtgg gactctgccc agcacccagc ctcacccacc    14280
cagtgcccat gctctgctct gagccatgtt gcgtccccca actctgctct gagctgtaga    14340
gccttggcac tttgagggtt aacaacagag ctgtcccctc ctcacctggc actggcagga    14400
ggccaagcca tagtgggtgg tgccagggga gcccctgtcc caggcagtgt tgcttagcca    14460
tgtcccttgg gggtgggggg gggtcactgc ctggtgctgt ccctgagcaa gggcaggaca    14520
gggacagctg tgacaggaag tactcatggc ccagccgttc ccatggagac ccccgctgcc    14580
cagcaactac accggctact gctgatgtca ggcagccaac tcctgttccc gtgggtgttc    14640
tgggcaggga gctggggcaa ggccaggggt ggtggctggt ttaggggcca gagtgaggtg    14700
gggaggggct gcatgagcgt gcttgtggat gtgagtgtgt gcctctatgt gaatacccca    14760
cacagaagct cgtccctcc ccctggcttt aaagcaaggt cttgcaggag gagggtgggt     14820
tcaggaccac cgggagcatg tgaagcttga gggggttctg aaggaagcaa tgtacccaat    14880
ttcatctgag gatagaggtg cccactgtag tagatttgtg tatccatgcc tatctgtgtg    14940
tgtgagaggg agagagagag agagttgatt gtgtcaatca attcaatgag gatggaggtt    15000
tcctcaaccc cacctgagga tagatttgca catttaagtc tgtctggaga tagatgaggc    15060
agtgtgtaga tgagtgtgtg tttgtgcacc tgtctgaggg cagatttggt gggtgtgtaa    15120
gaagagcact gggggggtagg tgacgctgga aggaatgtgt ctatttaggg cttggtggct    15180
catgcctgta attccaacac tctgggaggc tgaggcaggc agattgcttg aactcaggag    15240
ttcaagacca gcctgggcaa catggcttaa accccatctc tacaaaaaaa tataaaaaat    15300
tagccaggca tggtagtgca tgcctatagt cacagatatt tgggagtctg aggtgggagg    15360
attgcctgag cctgggaaat tgaggctgca gtgagccaag atcacaccac tgcactccag    15420
cctgggtgac aggagtgaga ccctgtcttg aaaaaaaaaa ggataaggct gggtgcggtg    15480
gctcatgctt gtaatcccaa cactttggga ggtcaaggtg ggtggatcac ctgaggtcag    15540
```

-continued

```
gagttcaaga ccagcctggt caacctggtg aaaccccatc tctactaaaa atccaaaaat    15600
taaccagata tggtggtggg cgcctgtaat cccagctact cgggaggctg aggcaaaaga    15660
attgcttgaa cccgggaggt ggaggttgca gtaagccgag attgcgccat tgcactccag    15720
cctgggtgac aagagcaaga ctccatctca aaacaaagaa aaagaaaaag aaaaaagata    15780
gattatgtgt gtgtgcgtgt gcgtgtgtac agtaggccag taggtcgatg gtgggagggc    15840
atgtgtctct ttgagggtgt gtgtgcctgt gagttcagcg gtcaggaagg ggcgcatact    15900
cctgtcctga ggtggggtgt agatgccagt gggaggccat gaagcagagc tttgcagagg    15960
ctgtatgtct gacaattgtc cttccccgct ccctcctaca gaccttcgcc ctttgcctga    16020
tgtcgccatg acaggcacat gtacccggga gtgcagtgag tttggccact ctgacacatg    16080
ctggatgcct ggcagtcat ctcccagccg ccggaccaag agcagcgccc tcaaactctc     16140
caccttcgtg ccttaccagg accgaggagg gcaggagcct gcgggcgccg gcagccccag    16200
ccccccggaa gaccggaaca ccaaaacggc cccgtgcgc ctcctgccct cctacagtgc     16260
cttctcccac agtagccatg attcctgcaa ggactcggcc accttggagg aaatccccct    16320
gacccagacc tcggacttcc cacccgcagc cacaccggca tctgcccaga cggccaagcg    16380
cgagatctac ctgtgagccc cctactggcc ggccggcccc cctcccccag ccgccggcca    16440
gctcccaaat ggcccattcc aggggcctca ctctccaccc cttcagcgtg gacttcctgg    16500
ccagggcccc aagtgggggt atcactgacc tcatgaccac gctggcccctt ctcccatgca   16560 gggtccaggt cctctcccct catttccatc tcccagcccc caggggcccc ttccccttta    16620 tgggcttcc cccagctgat gcccaagagg gctcctctgc aatgactggg ctccttccct     16680
tgacttccag ggagcacccc ctcgatttgg gcagatggtg gagtcaaggg tgggcagcgt    16740
acttctaact cattgtttcc ctcatggccg accagggcgg ggatagcatg cccaattttta    16800 gccctgaagc agggctgaac tggggagccc ctttccctgg gagctcccag aggaaactct    16860
tgaccaccag tggctccctg aagggctttt gttaccaaag gtggggtagg gacgggggtg    16920
ggagtggagc ggaggccttg ttttcccgtg ctgctcctgg actggcccac ctgcctgcca    16980
catgcccacg cctagtccca tctgggcccc cattccctgc tggtcatgca gtgtctgtat    17040
ataaggacct tggaatgacg tccccatttc tgcctgattt gcaacttttc ttgttgatgt    17100
cgtgttgtct tggggaccc ctctgggggg ggacctgccc tgtgcccct cctccctgcc      17160 gcagtgcccc ccaacccagg cctctattgt tccatgttgt aaatacccct ggggccatgg    17220
tgggatgggg gtgcaggcca gggaaacaac gggtgggtgg gggtggggac gggggtaaca    17280
tttgcctatc agcagagctg ggcttttatt taattttct taaaaataca aatctctatt     17340 tttttgaac tgttgcgctg tgcctgggg ggatccccgc tcaggctggc ctcccacatc      17400
cagatgagca tcacagaggg gccctgaggc tgtgggggc agctggacag gggtgggatg     17460
actgtgcctc tggcctggtt gggtgagttg ggagcaggaa ggtttgctca gggggtggct    17520
gggtgctgct cccgatatag ggggcctgca tcctgccccc tccctgccct ctcaacccccc   17580 agcccctgcc atgactgacc cgtcagcctg taaaaccacc attgccttga tctcaggggg    17640
tgggagggct gcctcagggc accctgggct ccaggccccc ttcttccagt tgggcttccc    17700
tttgtcaggg tcagggtcc catggggag ggggtaggga ggttgggggg cagagaagcc      17760
cagtcagcca tgatgaggtg aagttctctt cttcacctca gggggccagg gtgtaagggg    17820
cgtcctgcag agccccgtc tcccactgtg gccatctcaa agcctcagcc ctcttcctt      17880 ccagaaaccc ccactgcctt ggcccatacc tctccagctc cctaggggcc caggctggga    17940
```

```
ggctggagac tcagggtatg gcccttgctt gacttagtct aagcttgggg aggtggtcca    18000
agattgcgag cggtgggtac aggctgcggg gtcgtctggt gcctttggga gctgtgctgc    18060
tggggtcttg actcttgtac cccagagacc ccaccccac cccggaaaag ccagggggcct    18120 gaagaatcac cctatttatc tgcccccttac ccccaacttg gcttggggtg acagtgctag    18180
gaaggagagc attgttaggc tggtagccct ggcatacgaa gcccttctac agaggggaag    18240
gggtagaatg ggatggggtg gcagcagcca ggtctagggg ttggccaaag gctccctttcc   18300 cttgggagg cccaggagat gggcttgggg cttgttaaag agacagcccc tttcccctgc     18360
acaaatgggg caggtgcaat agtcttggag ttggtagtat tgggtgccca gctggtggaa    18420
cagtggcctc aaggattgtc ctgggtcctg gaggtcagga ttcgggcaag aagattgtat    18480
gaggcccatt tgcttggtgg agaaggtggt ccagacaggc ggcattcctg gggtcagtgg    18540
actcccactg gaagccccta gtggcctggg taccttgccc tggtcttaga gacccctgag    18600
cactgagcag aagagcagag gagcattttg cacaatggag aagccagaag aaagagggtg    18660
gcccagatgg ctgggagagc tgagaagccc ttcccacagg caaagacaga gcccccagcc    18720
ccctggttgg ggccagggca ctgagtctgt caccaactgg gcactggaga gatgaaacca    18780
aaggtgggca ggggttggcg acagcactgg ggactatccc tgtgggtcct aggtctgtga    18840
agcccctccc caatgcctgt gtcgcgtaca gttttatgta ccaataggcg acatttggcc    18900
agaggagagc cccctcaaa cccagcctga cccagtctgt gtcttcccag aggggaccta     18960
gtcggtcccc atccccctac ttcagggcat gtctctccgt agggggaggg tatatgggga    19020
catatttctc tcctagggtc cttgaagcat gttctcacatt ccggggtggg gggaagttct    19080
ctgggcatcc ctcacctctg gggtctctct aggccctatc tctccccttg ggagtctccg    19140
ggggacatgt gttcccgctg aggaccacgg gagcatgtct cccccaatta cccaggctct    19200
ctggggagcc tgttttcctc ccaggggttcc tgggagtact taaggcaagt cagtttcggg    19260
ccatctctct tcccagggaa gggggctatc tctgaaacac gtctgggaag ggatgtttct    19320
ggccctaccc ccatctctcc tatgggggtt tctctgccct gcagcacttt aggatgaggc    19380
tgggcatctc tgagttgtct ttctcctag gagccctggg atacctctct ctcccgaggg    19440
tagggcctct ggagccattt cttccctggg tcgggctgt ctccgggtgt tgggagggct    19500
tgtgttggcc atgagaaagt ctcttaaggg gcgtctccac tggggacttc tctgggaggg    19560
gggactgtgt cccgcccatg gggtttcggg cgggtgtgtc tgcccatggg gaggggagac    19620
tgtgtctcct cgggttatct agtggggagg ggggccgtgt ctctctcgtg tgtaggggggg    19680 cgtttgccct gctggctctt gtcttgcttg tccctctgc ttctctcccc gcctctcttc    19740
ccgtctgtgt ccctcctctc t                                              19761

<210> SEQ ID NO 2
<211> LENGTH: 2828
<212> TYPE: DNA
<213> ORGANISM: Homo sapiens

<400> SEQUENCE: 2 cggggaggt atatactacg cttggaaaaa ccagaggtgc attggtggga tacagacata       60
taggatttgc aaagggatat cctaagccaa gaacacattt tgctgtgcaa taacaggtat     120
agaagatatc ctaaaagacc acctgggcaa tgtccaattt tttagagaat ataaagtgga     180
ttgtgagtct atactcataa gaaatttagt actatgaagc cttctgtaag gtaatcccct     240
aaagaaataa ccctaagtat cttatccaag agtagtaagg acatatcttg aaagcattat     300
```

-continued

```
cattaccata cgatcaaggc cctgtcaacc tggtgattgc aatggcagtg tgctggccat    360
gataaagtct cctacgtggc atctccagtg gtgacttctc tgccagggta gactgtgtta    420
cgatcatgtg gcattggaat gagtgagtct accattatga agaaaagact gtgtctagtc    480
aggttttata taggtagggg tacagagtct ctatcgtgtg taagcgggta ggggtcagtg    540
taagggtttt gggcgcgtc gggtgcccac attggggtcg tgtttctctt ggttcgtgcc     600
acttcccact gcctcgctcc tcccgggaag ggccccgcc ccgccccacc ccaccccatc     660
cctggcgctg cgagcacaat cccgttgatt tgtaatgatt tctgtctctt tctgtctttc    720
tctttctctg acccccccac cccacccccc acccccccc acccgccgc gagcatgcgc      780
aggcaccgcc cctacccct ccggttcggt tcgtttccgg tttgtttgct gagctgtcaa     840
tgaaagaccc gtgtaattat tcccgagctt tacaataaaa gtgtgaaaac cggaccccac    900
tcagcttctt ccgggtcctc gggcctgcgt cccgtggaga gtgggagcta atctggagg     960
ccttggagag ggctggggga cgcgagggac aagagactga gacccgcact ggtattaatc   1020
ggggatgggg tcgagctgac gcgttctgag gatagactcc tagtccgtac acctcaaagt   1080
gaccctgcc ggatcctctg ggcccgacct gctgtgggca ccccctcccc gcaagaactc    1140
aggtgcagga tggggtggga ggtgaccgca ggagaggttt tgtgctgcgc tgccttcttc   1200
cccgggcgcc cgcaggacgt gcagtcgttc ccgggtgtat ccattcccgc tccccactct   1260
ttggcaacga gtgtgaattg cggaactgga taggataagg ggcgggagac atctgtctgt   1320
ctgccgcgtt ctcccacgct caggaacgag ggttggaagt cgatttaggg gaaaggaacc   1380
gaaaaggtct cagcctcggt ctccgactgc gctcccctcc cccttccgg gctcgaccgg    1440
ccccggcctc ctccgtccgg ctcccgggta acacccgct ccggagaggt cggaaaacag    1500
agaccggatc agccggttcc tggccccgcc tcccggggcg ttgctccctc ctccgcccct   1560
ccccacccc acaccgccc agcgtcgcgc gcttttggct cgaccgcgc cctagctccc     1620
taggccggta ctgtgtgggc ctcgctccgg acccgggt cggtccagcc gctgggatta     1680
gccgaccgca gggactaatc ccggatgagc ctcgtgtaaa cccggatcga cagcggggac   1740
ggcgggggtt gctggcaccc cttcatccgt tcccagacgc ggagcatcac ggggcataga   1800
gcccaccccg aggctccttg ctgctttcgg agagacccga gttggatctg cagttggggg   1860
cgtggcgggg caggagatga agaacgcagg gccgggatct gacgcgccga gagcctggcg   1920
cggggtgact gggtgtggg gcggaaaggc agagatctct cggcagtac ttgaatctac     1980
cggcttaggt cagctcccta ctcagtctac aaccgaagcc ccctaccat cctccagtta    2040
cagaatcaca gaccctcccc ctaccagtgg gtgtggcaac ccttcctaaa cctgaggcct   2100
cacctcatta ggagaggcgc tgaatcagcg ggggagggc ccgcattgtc tccacccctg    2160
acttgacccc acagtgaagg gtgaggagtt ccttctgtta aggcctagcc caggaaaaga   2220
tgtctggagt taaggaagtt ggaggagatg tggtggccga ctgggtacca gaatcctgtc   2280
actggttgat taactcattc tacaaacatt tcctgagccc ctcccatgtg ccagaccggc   2340
acagggtact ggaccccaag aatgacacac agtctctgtg ggaaaggcag acaggtaaac   2400
aatgaccaca tcttgtgttc ggccctgcct tgagccggaa attctggcag gagacctaaa   2460
ggcgctgtcc tctccaaagt ctagaggctt tctggaaggg gtggtgccag agctgagttt   2520
caaaggggcaa atgagggata ggctactgag gaagggtca gccttgcagg ctgaggagga   2580
gtatgtgcca gggtctggag gtggaggagg aggtgaggtg gctcaggagg caggagaag    2640
ttggagaaga aggcagggc cagaactaag gacctgctgg tcaacttaaa gtgcttggat    2700
```

-continued

| | |
|---|---|
| tgaggggttg gagaggagcc atttacagat tttaagcctg taaaagaaaa ggtcagattt | 2760 |
| acattcttcc agattctgtg ttcctcccct ccctgcccca ggtttctctg gggatgcctg | 2820 |
| ggttggga | 2828 |

<210> SEQ ID NO 3
<211> LENGTH: 2717
<212> TYPE: DNA
<213> ORGANISM: Homo sapiens

<400> SEQUENCE: 3

| | |
|---|---|
| gcatgagcca ctgtgcccag ccctaaattc atctttaaat gtaggaaaat agaaatagtg | 60 |
| tgtatttact gtgtccagac ctcctaatga ttagtatttc cacagactct gctttaagtc | 120 |
| gttggacagc ccagctccag ggccctgaat ctgtatcctc agacagttga tgcttattta | 180 |
| gtgaagcttc tggtctctgc attcaggaaa gggtaacagg gagaggaaga taacaaggat | 240 |
| aagagggaac tatggctgta atttaaactt tgaataaatg tttagaaaga ttggagaagt | 300 |
| cgtttgcttc ttttttaagg aaactcgctc aagatagttt gtttatagag ctggattttt | 360 |
| tttttctctt atactttcat ccattctccc ctgctctttg tagaggtgta tctatcatat | 420 |
| acaaacctga aattggtgta tattgataaa gttgctgtat tttggcagtg atattcctgt | 480 |
| gtgtgttttg gttctttctc tactatgta tgaatatcat taaatatata ttgaattatt | 540 |
| tgggtatttc ttttgacaaa attctacatc agagaccttt aagaaaaatc agaattcaat | 600 |
| ctattataggg tacatagggga agaagatgtt gtaaatagag aactggctta aggcaaataa | 660 |
| aagttggaat gggtaaagtt acttttcagt tatcttggtt actagtgtga tattttccta | 720 |
| agattctgaa agaggataat gagatatgta atttttagat ttgcaaaaag cacaggtttt | 780 |
| tctggctgga aaatgtccag ctgaaggtga taattagtat gaatctctca catgggaatg | 840 |
| caaatgagta agtgaaccac ttggagaaat gtaagtcaaa taagatgtta tgtccatttc | 900 |
| tggctatcac taatgattaa gagtaaaacc tcgagtcatc ataaactgtg tgccaaaagt | 960 |
| gcctaatatt tttctgtatg catagtgaat agcaagatga ctaacctctt taaagagggc | 1020 |
| acttttatat agaatcatac agtctacatc ttgtactagg tgtgaaggtg accatttttca | 1080 |
| cctctaaaac atttattagt gcttaagaaa atggctagag aaacataatg ggatgtaatg | 1140 |
| atgcctcttt aggattttct gaacattctt cagtctggaa aggtaaggac caaggaagca | 1200 |
| gtatgactaa tgtattagtc catcttgcat tgctatagag aaatacctga gactgggtaa | 1260 |
| tttgtaaaga aaagagggttt aattggctca tggtttggca ggctatacag gaagcatggc | 1320 |
| agtgtctgtt tctgggaggc ctcattcata gaactttaaa tcatggcaga aggcaaaggg | 1380 |
| gaagcgaggc ggcttacatg gcaggagcag ggtgccgggg ctgtgcactt ttaaacagat | 1440 |
| ctcatgagaa ctctatcata agaatagcac caaagggatg gtgctaaccc attcatgaag | 1500 |
| aatccacccc catgatccag tcacctccca ccaggcccca cttctaacgc tggggattac | 1560 |
| aattcgacat gagacttggt ggggacgcaa atccaaatca tatcaactaa agttaacaga | 1620 |
| atcacgaagt ggcgatagtg ttaccttgtt tgttgtgtga tgctgggatg cggaggggggc | 1680 |
| atttctgggt attggaaaga gaaagtcaag ttcattgggt gaattgaaaa catgaaaatc | 1740 |
| tcatatcctg aatgttgcat agattttaaa aggtttaatt aaattgatag atgatagatc | 1800 |
| catcatgaaa ggtaaattta aggggtgggg gacattctga atgtttttag gacaatgtca | 1860 |
| gtaaagggca gtgctcaccc aagagacata tattggtatc actgtcagaa tatagggccg | 1920 |
| gatgaactgt tgtgcttgtg aattattggg ttacattatt gaattgtgac ccatttaatg | 1980 |

-continued

| | |
|---|---|
| acgtgttctg cttagcgtct ttaggcccca cctaactctt ccagctctct attcgacatt | 2040 |
| ctctttggat tgttttgcta taacttgaaa tttgggatgt cacaaacgaa actgtcatct | 2100 |
| gtttccgcca aactgtggtt ctgctaatct cccaggctgg cagcattgga gacttgctga | 2160 |
| cttctttcat cccccactct tttcacctga aattcctttc cttggttttg ctctaagtcc | 2220 |
| tatgcttcag tcaggggcca accaaatctc actgcctcct ttttatcatg aagcctttga | 2280 |
| tcactgatag ttcttttat atcttgaaaa atcacccttc ccagtacagt taatatttag | 2340 |
| tatctctact catcttggca cttactcaca gctccataat tcagtgtttc tcgtacctct | 2400 |
| tcatggtgat ggggagccct ttggaggtgg tgactgtgct ttatactcct catgatgctt | 2460 |
| cacatgtggc aggcatggag tgaagacttt ttagaacaga atgctttaaa tggcatgtgg | 2520 |
| cctgaggaga tgattgtctt gtacctcttg ctaaaagtgg ttttcattct ttgtaggttt | 2580 |
| catgtggaca aactctcttc ggctcatgta taccttcgat tacataaggt aactgaattt | 2640 |
| aaacatggat tcttgacttt tctcctgatg atgcatcata tcttgttctt tatcctttgc | 2700 |
| aattaaattg cttacag | 2717 |

<210> SEQ ID NO 4
<211> LENGTH: 4069
<212> TYPE: DNA
<213> ORGANISM: Homo sapiens

<400> SEQUENCE: 4

| | |
|---|---|
| ctctattcga cattctcttt ggattgtttt gctataactt gaaatttggg atgtcacaaa | 60 |
| cgaaactgtc atctgttttcc gccaaactgt ggttctgcta atctcccagg ctggcagcat | 120 |
| tggagacttg ctgacttctt tcatccccca ctcttttcac ctgaaattcc tttccttggt | 180 |
| tttgctctaa gtcctatgct tcagtcaggg gccaaccaaa tctcactgcc tccttttat | 240 |
| catgaagcct ttgatcactg atagttcttt ttatatcttg aaaaatcacc cttcccagta | 300 |
| cagttaatat ttagtatctc tactcatctt ggcacttact cacagctcca taattcagtg | 360 |
| tttctcgtac ctcttcatgg tgatggggag ccctttggag tggtgactg tgctttatac | 420 |
| tcctcatgat gcttcacatg tggcaggcgt ggagtgcccg gaggcggccc tcctgattct | 480 |
| ggggcctccc aggatggagc ccctgaggca cagcccaggc cctgggggc aacggctact | 540 |
| gctgccctcc atgctgctag cactgctgct cctgctggcc ccatcccag ccacgccac | 600 |
| tcgggtagtg tacaaggtgc cggaggaaca gccacccaac accctcattg ggagcctcgc | 660 |
| agccgactat ggttttccag atgtgggca cctgtacaag ctagaggtgg gtgccccgta | 720 |
| ccttcgcgtg gatggcaaga caggtgacat tttccaccac gagacctcca tcgaccgtga | 780 |
| ggggctccgt gaatgccaga accagctccc tggtgatccc tgcatcctgg agtttgaggt | 840 |
| atctatcaca gacctcgtgc agaatgcgag cccccggctg ctagagggcc agatagaagt | 900 |
| acaagacatc aatgacaaca cacccaactt cgcctcacca gtcatcactc tggccatccc | 960 |
| tgagaacacc aacatcggct cactcttccc catcccgctg gcttcagacc gtgatgctgg | 1020 |
| tcccaacggt gtggcatcct atgagctgca ggtggcagag gaccaggagg agaagcaacc | 1080 |
| acagctcatt gtgatgggca acctggaccg tgagcgctgg gactcctatg acctcaccat | 1140 |
| caaggtgcag gatggcggca gccccccacg cgccacgagt gccctgctgc gtgtcaccgt | 1200 |
| gcttgacacc aatgacaacg cccccaagtt tgagcggccc tcctatgagg ccgaactatc | 1260 |
| tgagaatagc cccataggcc actcggtcat ccaggtgaag gccaatgact cagaccaagg | 1320 |
| tgccaatgca gaaatcgaat acacattcca ccaggcgccc gaagttgtga ggcgtcttct | 1380 |

```
tcgactggac aggaacactg gacttatcac tgttcaggc  ccggtggacc gtgaggacct    1440
aagcaccctg cgcttctcag tgcttgctaa ggaccgaggc accaacccca agagtgcccg    1500
tgcccaggtg gttgtgaccg tgaaggacat gaatgacaat gcccccacca ttgagatccg    1560
gggcataggg ctagtgactc atcaagatgg gatggctaac atctcagagg atgtggcaga    1620
ggagacagct gtggccctgg tgcaggtgtc tgaccgagat gagggagaga atgcagctgt    1680
cacctgtgtg gtggcaggtg atgtgccctt ccagctgcgc caggccagtg agacaggcag    1740
tgacagcaag aagaagtatt tcctgcagac taccaccccg ctagactacg agaaggtcaa    1800
agactacacc attgagattg tggctgtgga ctctggcaac cccccactct ccagcactaa    1860
ctccctcaag gtgcaggtgg tggacgtcaa tgacaacgca cctgtcttca ctcagagtgt    1920
cactgaggtc gccttcccgg aaaacaacaa gcctggtgaa gtgattgctg agatcactgc    1980
cagtgatgct gactctggct ctaatgctga gctggtttac tctctggagc ctgagccggc    2040
tgctaagggc ctcttcacca tctcacccga gactggagag atccaggtga agacatctct    2100
ggatcgggaa cagcgggaga gctatgagtt gaaggtggtg gcagctgacc ggggcagtcc    2160
tagcctccag ggcacagcca ctgtccttgt caatgtgctg gactgcaatg acaatgaccc    2220
caaatttatg ctgagtggct acaacttctc agtgatggag aacatgccag cactgagtcc    2280
agtgggcatg gtgactgtca ttgatggaga caaggggga aatgcccagg tgcagctctc    2340
agtggagcag acaacggtg actttgttat ccagaatggc acaggcacca tcctatccag    2400
cctgagcttt gatcgagagc aacaaagcac ctacaccttc cagctgaagg cagtggatgg    2460
tggcgtccca cctcgctcag cttacgttgg tgtcaccatc aatgtgctgg acgagaatga    2520
caacgcaccc tatatcactg ccccttctaa cacctctcac aagctgctga ccccccagac    2580
acgtcttggt gagacggtca gccaggtggc agccgaggac tttgactctg tgtcaatgc    2640 cgagctgatc tacagcattg caggtggcaa cccttatgga ctcttccaga ttgggtcaca    2700
ttcaggtgcc atcaccctgg agaaggagat tgagcggcgc accatgggc tacaccgcct    2760 ggtggtgaag gtcagtgacc gcggcaagcc cccacgctat ggcacagcct tggtccatct    2820
ttatgtcaat gagactctgg ccaaccgcac gctgctggag accctcctgg ccacagcct    2880 ggacacgccg ctggatattg acattgctgg ggatccagaa tatgagcgct ccaagcagcg    2940
tggcaacatt ctctttggtg tggtggctgg tgtggtggcc gtggccttgc tcatcgccct    3000
ggcggttctt gtgcgctact gcagacagcg ggaggccaaa agtggttacc aggctggtaa    3060
gaaggagacc aaggacctgt atgcccccaa gcccagtggc aaggcctcca agggaaacaa    3120
aagcaaaggc aagaagagca gtcccccaaa gcccgtgaag ccagtggagg acgaggatga    3180
ggccgggctg cagaagtccc tcaagttcaa cctgatgagc gatgccctg gggacagtcc    3240 ccgcatccac ctgccctca actacccacc aggcagccct gacctgggcc gccactatcg    3300
ctctaactcc ccactgcctt ccatccagct gcagccccag tcaccctcag cctccaagaa    3360
gcaccaggtg gtacaggacc tgccacctgc aaacacattc gtgggcaccg ggacaccac    3420 gtccacgggc tctgagcagt actccgacta cagctaccgc accaacccc caaataccc    3480 cagcaagcag gtaggccagc cttcagct cagcacaccc cagcccctac ccacccccta    3540 ccacggagc atctggaccg aggtgtggga gtgatggag aggtttactg tgcctgcccg    3600
tgttgggggc cagcctgagc cagcagtggg aggtgggccc ttagtgcctc accgggcaca    3660
cggattaggc tgagtgaaga ttaagggagg gtgtgctctg tggtctcctc cctgccctct    3720
ccccactggg gagagacctg tgatttgcca agtccctgga ccctgaccca gctactgggc    3780
```

-continued

```
cttatggstt gsgsstgsta sscasstsas catsaastsss saaseaaats ggtaagaagt   3840 ctactccaaa cctaggtctc tatgtcagac cagacctagg tgcttctcta ggagggaaac   3900
agggagacct gggstcctst ggataactga gtgsggagtc tgccaggsga sggcaccttc   3960
ccattgtgcc ttctgtgtgt attgtgcatt aacctcttcc tcaccactag gcttctgggg   4020
ctgggtccca catgcccttg accctgacaa taaagttctc tattttgg                4069

<210> SEQ ID NO 5
<211> LENGTH: 4649
<212> TYPE: DNA
<213> ORGANISM: Homo sapiens

<400> SEQUENCE: 5
ctctattcga cattctcttt ggattgtttt gctataactt gaaatttggg atgtcacaaa     60
cgaaactgtc atctgttccc gccaaactgt ggttctgcta atctcccagg ctggcagcat    120
tggagacttg ctgacttctt tcatccccca ctcttttcac ctgaaattcc tttccttggt    180
tttgctctaa gtcctatgct tcagtcaggg gccaaccaaa tctcactgcc tccttttat    240 catgaagcct tgatcactg atagttcttt ttatatcttg aaaaatcacc cttcccagta     300
cagttaatat ttagtatctc tactcatctt ggcacttact cacagctcca taattcagtg    360
tttctcgtac ctcttcatgg tgatgsggag ccctttggag gtggtgactg tgctttatac    420
tcctcatgat gcttcacatg tggcaggcgt ggagtgcccg gaggcggccc tcctgattct    480
ggggcctccc aggatggagc ccctgaggca cagcccaggc cctgggggc aacggctact     540 gctgccctcc atgctgctag cactgctgct cctgctggct ccatcccag gccacgccac     600 tcgggtagtg tacaaggtgc cggaggaaca gccacccaac accctcattg ggagcctcgc    660
agccgactat ggttttccag atgtggggca cctgtacaag ctagaggtgg gtgccccgta    720
ccttcgcgtg gatggcaaga caggtgacat tttcaccacc gagacctcca tcgaccgtga    780
ggggctccgt gaatgccaga accagctccc tggtgatccc tgcatcctgg agtttgaggt    840
atctatcaca gacctcgtgc agaatgcgag ccccggctg ctagagggcc agatagaagt      900
acaagacatc aatgacaaca cacccaactt cgcctcacca gtcatcactc tggccatccc    960
tgagaacacc aacatcggct cactcttccc catcccgctg gcttcagacc gtgatgctgg   1020
tcccaacggt gtggcatcct atgagctgca ggtggcagag gaccaggagg agaagcaacc   1080
acagctcatt gtgatgggca acctggaccg tgagcgctgg gactcctatg acctcaccat   1140
caaggtgcag gatggcggca gcccccacg cgccacgagt gccctgctgc gtgtcaccgt    1200
gcttgacacc aatgacaacg ccccaagtt tgagcggccc tcctatgagg ccgaactatc    1260
tgagaatagc cccataggcc actcggtcat ccaggtgaag gccaatgact cagaccaagg   1320
tgccaatgca gaaatcgaat acacattcca ccaggcgccc gaagttgtga ggcgtcttct   1380
tcgactggac aggaacactg gacttatcac tgttcagggc ccggtggacc gtgaggacct   1440
aagcaccctg cgcttctcag tgcttgctaa ggaccgaggc accaacccca gagtgccccg   1500
tgcccaggtg gttgtgaccg tgaaggacat gaatgacaat gcccccacca ttgagatccg   1560
gggcataggg ctagtgactc atcaagatgg gatggctaac atctcagagg atgtggcaga   1620
ggagacagct gtgccctgg tgcaggtgtc tgaccgagat gagggagaga atgcagctgt    1680
cacctgtgtg gtggcaggtg atgtgccctt ccagctgcgc caggccagtg agacaggcag   1740
tgacagcaag aagaagtatt tcctgcagac taccaccccg ctagactacg agaaggtcaa   1800
agactacacc attgagattg tggctgtgga ctctggcaac ccccactct ccagcactaa    1860
```

-continued

```
ctccctcaag gtgcaggtgg tggacgtcaa tgacaacgca cctgtcttca ctcagagtgt    1920
cactgaggtc gccttcccgg aaaacaacaa gcctggtgaa gtgattgctg agatcactgc    1980
cagtgatgct gactctggct ctaatgctga gctggtttac tctctggagc ctgagccggc    2040
tgctaagggc ctcttcacca tctcacccga gactggagag atccaggtga agacatctct    2100
ggatcgggaa cagcgggaga gctatgagtt gaaggtggtg gcagctgacc ggggcagtcc    2160
tagcctccag ggcacagcca ctgtccttgt caatgtgctg gactgcaatg acaatgaccc    2220
caaatttatg ctgagtggct acaacttctc agtgatggag aacatgccag cactgagtcc    2280
agtgggcatg tgactgtca ttgatggaga caaggggaga atgcccagg tgcagctctc    2340 agtggagcag gacaacggtg actttgttat ccagaatggc acaggcacca tcctatccag    2400
cctgagcttt gatcgagagc aacaaagcac ctacaccttc cagctgaagg cagtggatgg    2460
tggcgtccca cctcgctcag cttacgttgg tgtcaccatc aatgtgctgg acgagaatga    2520
caacgcaccc tatatcactg ccccttctaa cacctctcac aagctgctga cccccagac    2580 acgtcttggt gagacggtca gccaggtggc agccgaggac tttgactctg tgtcaatgc    2640 cgagctgatc tacagcattg caggtggcaa cccttatgga ctcttccaga ttgggtcaca    2700
ttcaggtgcc atcaccctgg agaaggagat tgagcggcgc caccatgggc tacaccgcct    2760
ggtggtgaag gtcagtgacc gcggcaagcc cccacgctat ggcacagcct ggtccatct    2820 ttatgtcaat gagactctgg ccaaccgcac gctgctggag accctcctgg ccacagcct    2880 ggacacgccg ctggatattg acattgctgg ggatccagaa tatgagcgct ccaagcagcg    2940
tggcaacatt ctctttggtg tggtggctgg tgtggtggcc gtggccttgc tcatcgccct    3000
ggcggttctt gtgcgctact gcagacacg ggaggccaaa agtggttacc aggctggtaa    3060
gaaggagacc aaggacctgt atgcccccaa gcccagtggc aaggcctcca agggaaacaa    3120
aagcaaaggc aagaagagca agtccccaaa gcccgtgaag ccagtggagg acgaggatga    3180
ggccgggctg cagaagtccc tcaagttcaa cctgatgagc gatgcccctg gggacagtcc    3240
ccgcatccac ctgcccctca actacccacc aggcagccct gacctgggcc gccactatcg    3300
ctctaactcc ccactgcctt ccatccagct gcagccccag tcaccctcag cctccaagaa    3360
gcaccaggtg gtacaggacc tgccacctgc aaacacattc gtgggcaccg ggacaccac    3420 gtccacgggc tctgagcagt actccgacta cagctaccgc accaaccccc caaataccc    3480 cagcaagcag ttacctcacc gccgcgtcac cttctcggcc accagccagg cccaggagct    3540
gcaggaccca tcccagcaca gttactatga cagtggcctg gaggagtctg agacgccgtc    3600
cagcaagtca tcctcagggc ctcgactcgg tccctggcc ctgcctgagg atcactatga    3660
gcgcaccacc cctgatggca gcataggaga gatggagcac cccgagaatg accttcgccc    3720
tttgcctgat gtcgccatga caggcacatg tacccgggag tgcagtgagt ttggccactc    3780
tgacacatgc tggatgcctg ccagtcatc tcccagccgc cggaccaaga gcagcgccct    3840
caaactctcc accttcatgc cttaccagga ccgaggaggg caggagcctg cgggcgccgg    3900
cagccccagc ccccggaag accggaacac caaaacggcc ccgtgcgcc tcctgccctc    3960 ctacagtgcc ttctcccaca gtagccatga ttcctgcaag gactcggcca ccttggagga    4020 aatcccctg acccagacct cggacttccc accgcagcc acaccggcat ctgcccagac    4080
ggccaagcgc gagatctacc tgtgagcccc ctactggccg gccccctcc cccagcgccg    4140 gccagctccc aaatgcccat tccagggcct cactctccac cccttcagcg tggacttcct    4200
gccagggccc aagtgggggt atcactgacc tcatgaccac gctggccctt ctcccatgca    4260
```

```
gggtccaggt cctctcccct catttccatc tcccagccca ggggcccctt ccccttt atg    4320 ggcttcccc cagctgatgc ccaagagggc tcctctgcaa tgactgggct ccttcccttg     4380
acttccaggg agcaccccct cgatttgggc agatggtgga gtcaagggtg ggcagcgtac    4440
ttctaactca ttgtttccct catggccgac cagggcgggg atagcatgcc caattttagc    4500
cctgaagcag gctgaactg gggagcccct ttccctggga gctcccagag gaaactcttg     4560
accaccagtg gctccctgaa gggcttttgt taccaaaggt ggggtaggga cggggtggg     4620 agtggagcgg aggccttgtt ttcccgtgg                                       4649

<210> SEQ ID NO 6
<211> LENGTH: 4684
<212> TYPE: DNA
<213> ORGANISM: Homo sapiens

<400> SEQUENCE: 6
ctctattcga cattctcttt ggattgtttt gctataactt gaaatttggg atgtcacaaa      60
cgaaactgtc atctgtttcc gccaaactgt ggttctgcta atctcccagg ctggcagcat    120
tggagacttg ctgacttctt tcatccccca ctcttttcac ctgaaattcc tttccttggt    180
tttgctctaa gtcctatgct tcagtcaggg gccaaccaaa tctcactgcc tccttttat    240 catgaagcct ttgatcactg atagttcttt ttatatcttg aaaaatcacc cttcccagta    300
cagttaatat ttagtatctc tactcatctt ggcacttact cacagctcca taattcagtg    360
tttctcgtac ctcttcatgg tgatggggag ccctttggag gtggtgactg tgctttatac    420
tcctcatgat gcttcacatg tggcaggcgt ggagtgcccg gaggcggccc tcctgattct    480
ggggcctccc aggatggagc ccctgaggca cagcccaggc cctgggggc aacggctact      540 gctgccctcc atgctgctag cactgctgct cctgctggct ccatcccag ccacgccac      600 tcgggtagtg tacaaggtgc cggaggaaca gccacccaac accctcattg ggagcctcgc    660
agccgactat ggttttccag atgtggggca cctgtacaag ctagaggtgg gtgccccgta    720
ccttcgcgtg gatggcaaga caggtgacat tttcaccacc gagacctcca tcgaccgtga    780
ggggctccgt gaatgccaga accagctccc tggtgatccc tgcatcctgg agtttgaggt    840
atctatcaca gacctcgtgc agaatgcgag ccccggctg ctagagggcc agatagaagt      900
acaagacatc aatgacaaca cacccaactt cgcctcacca gtcatcactc tggccatccc    960
tgagaacacc aacatcggct cactcttccc catcccgctg gcttcagacc gtgatgctgg   1020
tcccaacggt gtggcatcct atgagctgca ggtggcagag gaccaggagg agaagcaacc   1080
acagctcatt gtgatgggca acctggaccg tgagcgctgg gactcctatg acctcaccat   1140
caaggtgcag gatggcggca gcccccacg cgccacgagt gccctgctgc gtgtcaccgt   1200
gcttgacacc aatgacaacg cccccaagtt tgagcggccc tcctatgagg ccgaactatc   1260
tgagaatagc cccataggcc actcggtcat ccaggtgaag gccaatgact cagaccaagg   1320
tgccaatgca gaaatcgaat acacattcca ccaggcgccc gaagttgtga ggcgtcttct   1380
tcgactggac aggaacactg gacttatcac tgttcagggc ccggtggacc gtgaggacct   1440
aagcaccctg cgcttctcag tgcttgctaa ggaccgaggc accaacccca agagtgcccg   1500
tgcccaggtg gttgtgaccg tgaaggacat gaatgacaat gccccacca ttgagatccg    1560 ggcataggg ctagtgactc atcaagatgg gatggctaac atctcagagg atgtggcaga   1620
ggagacagct gtgccctgg tgcaggtgtc tgaccgagat gagggagaga atgcagctgt    1680
cacctgtgtg gtggcaggtg atgtgccctt ccagctgcgc caggccagtg agacaggcag   1740
```

```
tgacagcaag aagaagtatt tcctgcagac taccacccg ctagactacg agaaggtcaa    1800
agactacacc attgagattg tggctgtgga ctctggcaac cccccactct ccagcactaa   1860
ctccctcaag gtgcaggtgg tggacgtcaa tgacaacgca cctgtcttca ctcagagtgt   1920
cactgaggtc gccttcccgg aaaacaacaa gcctggtgaa gtgattgctg agatcactgc   1980
cagtgatgct gactctggct ctaatgctga gctggtttac tctctggagc ctgagccggc   2040
tgctaagggc ctcttcacca tctcacccga gactggagag atccaggtga agacatctct   2100
ggatcgggaa cagcgggaga gctatgagtt gaaggtggtg gcagctgacc ggggcagtcc   2160
tagcctccag ggcacagcca ctgtccttgt caatgtgctg gactgcaatg acaatgaccc   2220
caaatttatg ctgagtggct acaacttctc agtgatggag aacatgccag cactgagtcc   2280
agtgggcatg tgactgtca ttgatggaga caagggggag aatgcccagg tgcagctctc   2340
agtggagcag gacaacggtg actttgttat ccagaatggc acaggcacca tcctatccag   2400
cctgagcttt gatcgagagc aacaaagcac ctacaccttc cagctgaagg cagtggatgg   2460
tggcgtccca cctcgctcag cttacgttgg tgtcaccatc aatgtgctgg acgagaatga   2520
caacgcaccc tatatcactg cccccttctaa cacctctcac aagctgctga ccccccagac   2580
acgtcttggt gagacggtca gccaggtggc agccgaggac tttgactctg tgtcaatgc    2640 cgagctgatc tacagcattg caggtggcaa cccttatgga ctcttccaga ttgggtcaca   2700
ttcaggtgcc atcaccctgg agaaggagat tgagcggcgc caccatgggc tacaccgcct   2760
ggtggtgaag tcagtgacc gcggcaagcc cccacgctat ggcacagcct tggtccatct   2820
ttatgtcaat gagactctgg ccaaccgcac gctgctggag accctcctgg gccacagcct   2880
ggacacgccg ctggatattg acattgctgg ggatccagaa tatgagcgct ccaagcagcg   2940
tggcaacatt ctctttggtg tggtggctgg tgtggtggcc gtggccttgc tcatcgccct   3000
ggcggttctt gtgcgctact gcagacagcg ggaggccaaa agtggttacc aggctggtaa   3060
gaaggagacc aaggacctgt atgcccccaa gcccagtggc aaggcctcca agggaaacaa   3120
aagcaaaggc aagaagagca agtccccaaa gcccgtgaag ccagtggagg acgaggatga   3180
ggccgggctg cagaagtccc tcaagttcaa cctgatgagc gatgcccctg gggacagtcc   3240
ccgcatccac ctgcccctca actacccacc aggcagccct gacctgggcc gccactatcg   3300
ctctaactcc ccactgcctt ccatccagct gcagccccag tcaccctcag cctccaagaa   3360
gcaccaggtg gtacaggacc tgccacctgc aaacacattc gtgggcaccg gggacaccac   3420
gtccacgggc tctgagcagt actccgacta cagctaccgc accaacccc ccaaataccc   3480 cagcaagcag ttacctcacc gccgcgtcac cttctcggcc accagccagg cccaggagct   3540
gcaggaccca tcccagcaca gttactatga cagtggcctg gaggagtctg agacgccgtc   3600
cagcaagtca tcctcagggc ctcgactcgg tccctggcc ctgcctgagg atcactatga   3660
gcgcaccacc cctgatggca gcataggaga gatggagcac cccgagaatg accttcgccc   3720
tttgcctgat gtcgccatga caggcacatg tacccgggag tgcagtgagt ttggccactc   3780
tgacacatgc tggatgcctg ccagtcatc tcccagccgc cggaccaaga gcagcgccct   3840
caaactctcc accttcatgc cttaccagga ccgaggaggg caggagcctg cgggcgccgg   3900
cagccccagc ccccggaag accggaacac caaaacggcc ccgtgcgcc tcctgccctc   3960 ctacagtgcc ttctcccaca gtagccatga ttcctgcaag gactcggcca ccttggagga   4020 aatcccctg acccagacct cggacttccc accccgcagcc acaccggcat ctgcccagac   4080
ggccaagcgc gagatctacc tgtgagcccc ctactggccg gcccccctcc cccagcgccg   4140
```

-continued

```
gccagctccc aaatgcccat tccagggcct cactctccac cccttcagcg tggacttcct    4200
gccagggccc aagtgggggt atcactgacc tcatgaccac gctggccctt ctcccatgca    4260
gggtccaggt cctctcccct catttccatc tcccagccca ggggcccctt cccctttatg    4320
ggcttccccc agctgatgcc caagagggtc tctgcaatg actgggctcc ttcccttgac     4380
ttccagggag cacccctcg atttgggcag atggtggagt caagggtggg cagcgtactt      4440
ctaactcatt gtttccctca tggccgacca gggcggggat agcatgccca attttagccc    4500
tgaagcaggg tgaactgggg agccccttc cctgggagct cccagaggaa actcttgacc     4560
accagtggct ccctgaaggg cttttgttac cccctccggt tcggttcgtt tccggtttgt    4620
ttgctgagct gtcaatgaaa gacccgtgta attattcccg agctttacaa taaaagtgtg    4680
aaaa                                                                 4684
```

<210> SEQ ID NO 7
<211> LENGTH: 1065
<212> TYPE: PRT
<213> ORGANISM: Homo sapiens

<400> SEQUENCE: 7

```
Met Val Met Gly Ser Pro Leu Glu Val Val Thr Val Leu Tyr Thr Pro
  1               5                  10                  15

His Asp Ala Ser His Val Ala Gly Val Glu Cys Pro Glu Ala Ala Leu
             20                  25                  30

Leu Ile Leu Gly Pro Pro Arg Met Glu Pro Leu Arg His Ser Pro Gly
         35                  40                  45

Pro Gly Gly Gln Arg Leu Leu Leu Pro Ser Met Leu Leu Ala Leu Leu
     50                  55                  60

Leu Leu Leu Ala Pro Ser Pro Gly His Ala Thr Arg Val Val Tyr Lys
 65                  70                  75                  80

Val Pro Glu Glu Gln Pro Pro Asn Thr Leu Ile Gly Ser Leu Ala Ala
                 85                  90                  95

Asp Tyr Gly Phe Pro Asp Val Gly His Leu Tyr Lys Leu Glu Val Gly
            100                 105                 110

Ala Pro Tyr Leu Arg Val Asp Gly Lys Thr Gly Asp Ile Phe Thr Thr
        115                 120                 125

Glu Thr Ser Ile Asp Arg Glu Gly Leu Arg Glu Cys Gln Asn Gln Leu
    130                 135                 140

Pro Gly Asp Pro Cys Ile Leu Glu Phe Glu Val Ser Ile Thr Asp Leu
145                 150                 155                 160

Val Gln Asn Ala Ser Pro Arg Leu Leu Glu Gly Gln Ile Glu Val Gln
                165                 170                 175

Asp Ile Asn Asp Asn Thr Pro Asn Phe Ala Ser Pro Val Ile Thr Leu
            180                 185                 190

Ala Ile Pro Glu Asn Thr Asn Ile Gly Ser Leu Phe Pro Ile Pro Leu
        195                 200                 205

Ala Ser Asp Arg Asp Ala Gly Pro Asn Gly Val Ala Ser Tyr Glu Leu
    210                 215                 220

Gln Val Ala Glu Asp Gln Glu Lys Gln Pro Gln Leu Ile Val Met
225                 230                 235                 240

Gly Asn Leu Asp Arg Glu Arg Trp Asp Ser Tyr Asp Leu Thr Ile Lys
                245                 250                 255

Val Gln Asp Gly Gly Ser Pro Pro Arg Ala Thr Ser Ala Leu Leu Arg
            260                 265                 270
```

-continued

```
Val Thr Val Leu Asp Thr Asn Asp Asn Ala Pro Lys Phe Glu Arg Pro
            275                 280                 285

Ser Tyr Glu Ala Glu Leu Ser Glu Asn Ser Pro Ile Gly His Ser Val
            290                 295                 300

Ile Gln Val Lys Ala Asn Asp Ser Asp Gln Gly Ala Asn Ala Glu Ile
305                 310                 315                 320

Glu Tyr Thr Phe His Gln Ala Pro Glu Val Val Arg Arg Leu Leu Arg
            325                 330                 335

Leu Asp Arg Asn Thr Gly Leu Ile Thr Val Gln Gly Pro Val Asp Arg
            340                 345                 350

Glu Asp Leu Ser Thr Leu Arg Phe Ser Val Leu Ala Lys Asp Arg Gly
            355                 360                 365

Thr Asn Pro Lys Ser Ala Arg Ala Gln Val Val Thr Val Lys Asp
            370                 375                 380

Met Asn Asp Asn Ala Pro Thr Ile Glu Ile Arg Gly Ile Gly Leu Val
385                 390                 395                 400

Thr His Gln Asp Gly Met Ala Asn Ile Ser Glu Asp Val Ala Glu Glu
            405                 410                 415

Thr Ala Val Ala Leu Val Gln Val Ser Asp Arg Asp Glu Gly Glu Asn
            420                 425                 430

Ala Ala Val Thr Cys Val Val Ala Gly Asp Val Pro Phe Gln Leu Arg
            435                 440                 445

Gln Ala Ser Glu Thr Gly Ser Asp Ser Lys Lys Lys Tyr Phe Leu Gln
            450                 455                 460

Thr Thr Thr Pro Leu Asp Tyr Glu Lys Val Lys Asp Tyr Thr Ile Glu
465                 470                 475                 480

Ile Val Ala Val Asp Ser Gly Asn Pro Pro Leu Ser Ser Thr Asn Ser
            485                 490                 495

Leu Lys Val Gln Val Val Asp Val Asn Asp Asn Ala Pro Val Phe Thr
            500                 505                 510

Gln Ser Val Thr Glu Val Ala Phe Pro Glu Asn Asn Lys Pro Gly Glu
            515                 520                 525

Val Ile Ala Glu Ile Thr Ala Ser Asp Ala Asp Ser Gly Ser Asn Ala
            530                 535                 540

Glu Leu Val Tyr Ser Leu Glu Pro Glu Pro Ala Ala Lys Gly Leu Phe
545                 550                 555                 560

Thr Ile Ser Pro Glu Thr Gly Glu Ile Gln Val Lys Thr Ser Leu Asp
            565                 570                 575

Arg Glu Gln Arg Glu Ser Tyr Glu Leu Lys Val Val Ala Ala Asp Arg
            580                 585                 590

Gly Ser Pro Ser Leu Gln Gly Thr Ala Thr Val Leu Val Asn Val Leu
            595                 600                 605

Asp Cys Asn Asp Asn Asp Pro Lys Phe Met Leu Ser Gly Tyr Asn Phe
610                 615                 620

Ser Val Met Glu Asn Met Pro Ala Leu Ser Pro Val Gly Met Val Thr
625                 630                 635                 640

Val Ile Asp Gly Asp Lys Gly Glu Asn Ala Gln Val Gln Leu Ser Val
            645                 650                 655

Glu Gln Asp Asn Gly Asp Phe Val Ile Gln Asn Gly Thr Gly Thr Ile
            660                 665                 670

Leu Ser Ser Leu Ser Phe Asp Arg Glu Gln Gln Ser Thr Tyr Thr Phe
            675                 680                 685
```

```
Gln Leu Lys Ala Val Asp Gly Val Pro Arg Ser Ala Tyr Val
    690                 695                 700

Gly Val Thr Ile Asn Val Leu Asp Glu Asn Asp Ala Pro Tyr Ile
705                 710                 715                 720

Thr Ala Pro Ser Asn Thr Ser His Lys Leu Leu Thr Pro Gln Thr Arg
                725                 730                 735

Leu Gly Glu Thr Val Ser Gln Val Ala Ala Glu Asp Phe Asp Ser Gly
            740                 745                 750

Val Asn Ala Glu Leu Ile Tyr Ser Ile Ala Gly Gly Asn Pro Tyr Gly
        755                 760                 765

Leu Phe Gln Ile Gly Ser His Ser Gly Ala Ile Thr Leu Glu Lys Glu
    770                 775                 780

Ile Glu Arg Arg His His Gly Leu His Arg Leu Val Lys Val Ser
785                 790                 795                 800

Asp Arg Gly Lys Pro Pro Arg Tyr Gly Thr Ala Leu Val His Leu Tyr
                805                 810                 815

Val Asn Glu Thr Leu Ala Asn Arg Thr Leu Glu Thr Leu Leu Gly
            820                 825                 830

His Ser Leu Asp Thr Pro Leu Asp Ile Asp Ile Ala Gly Asp Pro Glu
        835                 840                 845

Tyr Glu Arg Ser Lys Gln Arg Gly Asn Ile Leu Phe Gly Val Val Ala
    850                 855                 860

Gly Val Val Ala Val Ala Leu Leu Ile Ala Leu Ala Val Leu Val Arg
865                 870                 875                 880

Tyr Cys Arg Gln Arg Glu Ala Lys Ser Gly Tyr Gln Ala Gly Lys Lys
                885                 890                 895

Glu Thr Lys Asp Leu Tyr Ala Pro Lys Pro Ser Gly Lys Ala Ser Lys
            900                 905                 910

Gly Asn Lys Ser Lys Gly Lys Lys Ser Lys Ser Pro Lys Pro Val Lys
        915                 920                 925

Pro Val Glu Asp Glu Asp Glu Ala Gly Leu Gln Lys Ser Leu Lys Phe
    930                 935                 940

Asn Leu Met Ser Asp Ala Pro Gly Asp Ser Pro Arg Ile His Leu Pro
945                 950                 955                 960

Leu Asn Tyr Pro Pro Gly Ser Pro Asp Leu Gly Arg His Tyr Arg Ser
                965                 970                 975

Asn Ser Pro Leu Pro Ser Ile Gln Leu Gln Pro Gln Ser Pro Ser Ala
            980                 985                 990

Ser Lys Lys His Gln Val Val Gln Asp Leu Pro Pro Ala Asn Thr Phe
        995                1000                1005

Val Gly Thr Gly Asp Thr Thr Ser Thr Gly Ser Glu Gln Tyr Ser Asp
   1010                1015                1020

Tyr Ser Tyr Arg Thr Asn Pro Pro Lys Tyr Pro Ser Lys Gln Val Gly
1025                1030                1035                1040

Gln Pro Phe Gln Leu Ser Thr Gln Pro Leu Pro His Pro Tyr His
                1045                1050                1055

Gly Ala Ile Trp Thr Glu Val Trp Glu
            1060                1065

<210> SEQ ID NO 8
<211> LENGTH: 1242
<212> TYPE: PRT
<213> ORGANISM: Homo sapiens
```

<400> SEQUENCE: 8

```
Met Val Met Gly Ser Pro Leu Glu Val Val Thr Val Leu Tyr Thr Pro
1               5                   10                  15

His Asp Ala Ser His Val Ala Gly Val Glu Cys Pro Glu Ala Ala Leu
            20                  25                  30

Leu Ile Leu Gly Pro Pro Arg Met Glu Pro Leu Arg His Ser Pro Gly
        35                  40                  45

Pro Gly Gly Gln Arg Leu Leu Leu Pro Ser Met Leu Leu Ala Leu Leu
    50                  55                  60

Leu Leu Leu Ala Pro Ser Pro Gly His Ala Thr Arg Val Val Tyr Lys
65                  70                  75                  80

Val Pro Glu Glu Gln Pro Pro Asn Thr Leu Ile Gly Ser Leu Ala Ala
                85                  90                  95

Asp Tyr Gly Phe Pro Asp Val Gly His Leu Tyr Lys Leu Glu Val Gly
            100                 105                 110

Ala Pro Tyr Leu Arg Val Asp Gly Lys Thr Gly Asp Ile Phe Thr Thr
        115                 120                 125

Glu Thr Ser Ile Asp Arg Glu Gly Leu Arg Glu Cys Gln Asn Gln Leu
130                 135                 140

Pro Gly Asp Pro Cys Ile Leu Glu Phe Glu Val Ser Ile Thr Asp Leu
145                 150                 155                 160

Val Gln Asn Ala Ser Pro Arg Leu Leu Glu Gly Gln Ile Glu Val Gln
                165                 170                 175

Asp Ile Asn Asp Asn Thr Pro Asn Phe Ala Ser Pro Val Ile Thr Leu
            180                 185                 190

Ala Ile Pro Glu Asn Thr Asn Ile Gly Ser Leu Phe Pro Ile Pro Leu
        195                 200                 205

Ala Ser Asp Arg Asp Ala Gly Pro Asn Gly Val Ala Ser Tyr Glu Leu
    210                 215                 220

Gln Val Ala Glu Asp Gln Glu Lys Gln Pro Gln Leu Ile Val Met
225                 230                 235                 240

Gly Asn Leu Asp Arg Glu Arg Trp Asp Ser Tyr Asp Leu Thr Ile Lys
                245                 250                 255

Val Gln Asp Gly Gly Ser Pro Pro Arg Ala Thr Ser Ala Leu Leu Arg
            260                 265                 270

Val Thr Val Leu Asp Thr Asn Asp Asn Ala Pro Lys Phe Glu Arg Pro
        275                 280                 285

Ser Tyr Glu Ala Glu Leu Ser Glu Asn Ser Pro Ile Gly His Ser Val
    290                 295                 300

Ile Gln Val Lys Ala Asn Asp Ser Asp Gln Gly Ala Asn Ala Glu Ile
305                 310                 315                 320

Glu Tyr Thr Phe His Gln Ala Pro Glu Val Val Arg Leu Leu Arg
                325                 330                 335

Leu Asp Arg Asn Thr Gly Leu Ile Thr Val Gln Gly Pro Val Asp Arg
            340                 345                 350

Glu Asp Leu Ser Thr Leu Arg Phe Ser Val Leu Ala Lys Asp Arg Gly
        355                 360                 365

Thr Asn Pro Lys Ser Ala Arg Ala Gln Val Val Thr Val Lys Asp
    370                 375                 380

Met Asn Asp Asn Ala Pro Thr Ile Glu Ile Arg Gly Ile Gly Leu Val
385                 390                 395                 400

Thr His Gln Asp Gly Met Ala Asn Ile Ser Glu Asp Val Ala Glu Glu
                405                 410                 415
```

```
Thr Ala Val Ala Leu Val Gln Val Ser Asp Arg Asp Glu Gly Glu Asn
            420                 425                 430

Ala Ala Val Thr Cys Val Val Ala Gly Asp Val Pro Phe Gln Leu Arg
            435                 440                 445

Gln Ala Ser Glu Thr Gly Ser Asp Ser Lys Lys Tyr Phe Leu Gln
    450                 455                 460

Thr Thr Thr Pro Leu Asp Tyr Glu Lys Val Lys Asp Tyr Thr Ile Glu
465             470                 475                 480

Ile Val Ala Val Asp Ser Gly Asn Pro Pro Leu Ser Ser Thr Asn Ser
                485                 490                 495

Leu Lys Val Gln Val Val Asp Val Asn Asp Asn Ala Pro Val Phe Thr
            500                 505                 510

Gln Ser Val Thr Glu Val Ala Phe Pro Glu Asn Asn Lys Pro Gly Glu
        515                 520                 525

Val Ile Ala Glu Ile Thr Ala Ser Asp Ala Asp Ser Gly Ser Asn Ala
    530                 535                 540

Glu Leu Val Tyr Ser Leu Glu Pro Glu Pro Ala Ala Lys Gly Leu Phe
545             550                 555                 560

Thr Ile Ser Pro Glu Thr Gly Glu Ile Gln Val Lys Thr Ser Leu Asp
                565                 570                 575

Arg Glu Gln Arg Glu Ser Tyr Glu Leu Lys Val Val Ala Ala Asp Arg
            580                 585                 590

Gly Ser Pro Ser Leu Gln Gly Thr Ala Thr Val Leu Val Asn Val Leu
    595                 600                 605

Asp Cys Asn Asp Asn Asp Pro Lys Phe Met Leu Ser Gly Tyr Asn Phe
        610                 615                 620

Ser Val Met Glu Asn Met Pro Ala Leu Ser Pro Val Gly Met Val Thr
625             630                 635                 640

Val Ile Asp Gly Asp Lys Gly Glu Asn Ala Gln Val Gln Leu Ser Val
                645                 650                 655

Glu Gln Asp Asn Gly Asp Phe Val Ile Gln Asn Gly Thr Gly Thr Ile
            660                 665                 670

Leu Ser Ser Leu Ser Phe Asp Arg Glu Gln Gln Ser Thr Tyr Thr Phe
    675                 680                 685

Gln Leu Lys Ala Val Asp Gly Gly Val Pro Pro Arg Ser Ala Tyr Val
    690                 695                 700

Gly Val Thr Ile Asn Val Leu Asp Glu Asn Asp Asn Ala Pro Tyr Ile
705             710                 715                 720

Thr Ala Pro Ser Asn Thr Ser His Lys Leu Leu Thr Pro Gln Thr Arg
                725                 730                 735

Leu Gly Glu Thr Val Ser Gln Val Ala Ala Glu Asp Phe Asp Ser Gly
            740                 745                 750

Val Asn Ala Glu Leu Ile Tyr Ser Ile Ala Gly Gly Asn Pro Tyr Gly
    755                 760                 765

Leu Phe Gln Ile Gly Ser His Ser Gly Ala Ile Thr Leu Glu Lys Glu
    770                 775                 780

Ile Glu Arg Arg His His Gly Leu His Arg Leu Val Val Lys Val Ser
785             790                 795                 800

Asp Arg Gly Lys Pro Pro Arg Tyr Gly Thr Ala Leu Val His Leu Tyr
                805                 810                 815

Val Asn Glu Thr Leu Ala Asn Arg Thr Leu Leu Glu Thr Leu Leu Gly
            820                 825                 830
```

```
His Ser Leu Asp Thr Pro Leu Asp Ile Asp Ile Ala Gly Asp Pro Glu
        835                 840                 845

Tyr Glu Arg Ser Lys Gln Arg Gly Asn Ile Leu Phe Gly Val Val Ala
    850                 855                 860

Gly Val Ala Val Ala Leu Leu Ile Ala Leu Ala Val Leu Val Arg
865                 870                 875                 880

Tyr Cys Arg Gln Arg Glu Ala Lys Ser Gly Tyr Gln Ala Gly Lys Lys
                885                 890                 895

Glu Thr Lys Asp Leu Tyr Ala Pro Lys Pro Ser Gly Lys Ala Ser Lys
            900                 905                 910

Gly Asn Lys Ser Lys Gly Lys Lys Ser Lys Ser Pro Lys Pro Val Lys
        915                 920                 925

Pro Val Glu Asp Glu Asp Glu Ala Gly Leu Gln Lys Ser Leu Lys Phe
    930                 935                 940

Asn Leu Met Ser Asp Ala Pro Gly Asp Ser Pro Arg Ile His Leu Pro
945                 950                 955                 960

Leu Asn Tyr Pro Pro Gly Ser Pro Asp Leu Gly Arg His Tyr Arg Ser
                965                 970                 975

Asn Ser Pro Leu Pro Ser Ile Gln Leu Gln Pro Gln Ser Pro Ser Ala
            980                 985                 990

Ser Lys Lys His Gln Val Val Gln Asp Leu Pro Pro Ala Asn Thr Phe
        995                 1000                1005

Val Gly Thr Gly Asp Thr Thr Ser Thr Gly Ser Glu Gln Tyr Ser Asp
    1010                1015                1020

Tyr Ser Tyr Arg Thr Asn Pro Pro Lys Tyr Pro Ser Lys Gln Leu Pro
1025                1030                1035                1040

His Arg Arg Val Thr Phe Ser Ala Thr Ser Gln Ala Gln Glu Leu Gln
                1045                1050                1055

Asp Pro Ser Gln His Ser Tyr Tyr Asp Ser Gly Leu Glu Glu Ser Glu
            1060                1065                1070

Thr Pro Ser Ser Lys Ser Ser Gly Pro Arg Leu Gly Pro Leu Ala
        1075                1080                1085

Leu Pro Glu Asp His Tyr Glu Arg Thr Thr Pro Asp Gly Ser Ile Gly
    1090                1095                1100

Glu Met Glu His Pro Glu Asn Asp Leu Arg Pro Leu Pro Asp Val Ala
1105                1110                1115                1120

Met Thr Gly Thr Cys Thr Arg Glu Cys Ser Glu Phe Gly His Ser Asp
                1125                1130                1135

Thr Cys Trp Met Pro Gly Gln Ser Ser Pro Ser Arg Arg Thr Lys Ser
            1140                1145                1150

Ser Ala Leu Lys Leu Ser Thr Phe Met Pro Tyr Gln Asp Arg Gly Gly
        1155                1160                1165

Gln Glu Pro Ala Gly Ala Gly Ser Pro Ser Pro Glu Asp Arg Asn
    1170                1175                1180

Thr Lys Thr Ala Pro Val Arg Leu Leu Pro Ser Tyr Ser Ala Phe Ser
1185                1190                1195                1200

His Ser Ser His Asp Ser Cys Lys Asp Ser Ala Thr Leu Glu Glu Ile
                1205                1210                1215

Pro Leu Thr Gln Thr Ser Asp Phe Pro Pro Ala Ala Thr Pro Ala Ser
            1220                1225                1230

Ala Gln Thr Ala Lys Arg Glu Ile Tyr Leu
        1235                1240
```

<210> SEQ ID NO 9
<211> LENGTH: 23
<212> TYPE: DNA
<213> ORGANISM: Homo sapiens

<400> SEQUENCE: 9
cttgccttag gcttatctcc ctt                                    23

<210> SEQ ID NO 10
<211> LENGTH: 22
<212> TYPE: DNA
<213> ORGANISM: Homo sapiens

<400> SEQUENCE: 10
gcctcggaat gtcagctact tt                                     22

<210> SEQ ID NO 11
<211> LENGTH: 19
<212> TYPE: DNA
<213> ORGANISM: Homo sapiens

<400> SEQUENCE: 11
ggtcatctgg tgcctttgg                                         19

<210> SEQ ID NO 12
<211> LENGTH: 22
<212> TYPE: DNA
<213> ORGANISM: Homo sapiens

<400> SEQUENCE: 12
ccagcctaac aatgctctcc tt                                     22

<210> SEQ ID NO 13
<211> LENGTH: 22
<212> TYPE: DNA
<213> ORGANISM: Homo sapiens

<400> SEQUENCE: 13
agtgtacaag gtgccggagg aa                                     22

<210> SEQ ID NO 14
<211> LENGTH: 22
<212> TYPE: DNA
<213> ORGANISM: Homo sapiens

<400> SEQUENCE: 14
agctcatagg atgccacacc gt                                     22

<210> SEQ ID NO 15
<211> LENGTH: 21
<212> TYPE: DNA
<213> ORGANISM: Homo sapiens

<400> SEQUENCE: 15
gtacactacc cgagtggcgt g                                      21

<210> SEQ ID NO 16
<211> LENGTH: 21
<212> TYPE: DNA
<213> ORGANISM: Homo sapiens

```
<400> SEQUENCE: 16
cctcctactg gctcctccag c                                             21

<210> SEQ ID NO 17
<211> LENGTH: 20
<212> TYPE: DNA
<213> ORGANISM: Homo sapiens

<400> SEQUENCE: 17
agctggcccc catactcacc                                               20

<210> SEQ ID NO 18
<211> LENGTH: 20
<212> TYPE: DNA
<213> ORGANISM: Homo sapiens

<400> SEQUENCE: 18
cgtccactgg ctctctctcc                                               20

<210> SEQ ID NO 19
<211> LENGTH: 16
<212> TYPE: DNA
<213> ORGANISM: Homo sapiens

<400> SEQUENCE: 19
tcccgcccat ggaaca                                                   16

<210> SEQ ID NO 20
<211> LENGTH: 24
<212> TYPE: DNA
<213> ORGANISM: Homo sapiens

<400> SEQUENCE: 20
gacttggcat ctcagaacaa agag                                          24

<210> SEQ ID NO 21
<211> LENGTH: 20
<212> TYPE: DNA
<213> ORGANISM: Homo sapiens

<400> SEQUENCE: 21
ctccccacat gcatggtagg                                               20

<210> SEQ ID NO 22
<211> LENGTH: 18
<212> TYPE: DNA
<213> ORGANISM: Homo sapiens

<400> SEQUENCE: 22
gcatgctctg gggcatgt                                                 18

<210> SEQ ID NO 23
<211> LENGTH: 23
<212> TYPE: DNA
<213> ORGANISM: Homo sapiens

<400> SEQUENCE: 23 tcctctttt ctgacaatca ccc                                            23

<210> SEQ ID NO 24
<211> LENGTH: 18
<212> TYPE: DNA
<213> ORGANISM: Homo sapiens
```

```
<400> SEQUENCE: 24
aaggacaggc cagggcag                                                    18

<210> SEQ ID NO 25
<211> LENGTH: 22
<212> TYPE: DNA
<213> ORGANISM: Homo sapiens

<400> SEQUENCE: 25
ttctggcagt ttttcccta ag                                                22

<210> SEQ ID NO 26
<211> LENGTH: 20
<212> TYPE: DNA
<213> ORGANISM: Homo sapiens

<400> SEQUENCE: 26
gagctatttg ggctgcaggt                                                  20

<210> SEQ ID NO 27
<211> LENGTH: 18
<212> TYPE: DNA
<213> ORGANISM: Homo sapiens

<400> SEQUENCE: 27
tcaagcacgg tgacacgc                                                    18

<210> SEQ ID NO 28
<211> LENGTH: 16
<212> TYPE: DNA
<213> ORGANISM: Homo sapiens

<400> SEQUENCE: 28
gcccccggct gctaga                                                      16

<210> SEQ ID NO 29
<211> LENGTH: 17
<212> TYPE: DNA
<213> ORGANISM: Homo sapiens

<400> SEQUENCE: 29
tgggaccagc atcacgg                                                     17

<210> SEQ ID NO 30
<211> LENGTH: 21
<212> TYPE: DNA
<213> ORGANISM: Homo sapiens

<400> SEQUENCE: 30
cagccgacta tggttttcca g                                                21

<210> SEQ ID NO 31
<211> LENGTH: 19
<212> TYPE: DNA
<213> ORGANISM: Homo sapiens

<400> SEQUENCE: 31
gatgcaggga tcaccaggg                                                   19

<210> SEQ ID NO 32
<211> LENGTH: 21
<212> TYPE: DNA
<213> ORGANISM: Homo sapiens
```

```
<400> SEQUENCE: 32
cttgcagcct tcctgattct g                                              21

<210> SEQ ID NO 33
<211> LENGTH: 21
<212> TYPE: DNA
<213> ORGANISM: Homo sapiens

<400> SEQUENCE: 33
cttgacacca atgacaacgc c                                              21

<210> SEQ ID NO 34
<211> LENGTH: 19
<212> TYPE: DNA
<213> ORGANISM: Homo sapiens

<400> SEQUENCE: 34
tcagaggttc ccccagctt                                                 19

<210> SEQ ID NO 35
<211> LENGTH: 21
<212> TYPE: DNA
<213> ORGANISM: Homo sapiens

<400> SEQUENCE: 35
tagtgagacc ccttctcccc a                                              21

<210> SEQ ID NO 36
<211> LENGTH: 23
<212> TYPE: DNA
<213> ORGANISM: Homo sapiens

<400> SEQUENCE: 36
ctttgtcagg aagaggcaaa atg                                            23

<210> SEQ ID NO 37
<211> LENGTH: 23
<212> TYPE: DNA
<213> ORGANISM: Homo sapiens

<400> SEQUENCE: 37
aggtgagctg agttggaaca aag                                            23

<210> SEQ ID NO 38
<211> LENGTH: 19
<212> TYPE: DNA
<213> ORGANISM: Homo sapiens

<400> SEQUENCE: 38
ccaagctgcc tagtgcctg                                                 19

<210> SEQ ID NO 39
<211> LENGTH: 21
<212> TYPE: DNA
<213> ORGANISM: Homo sapiens

<400> SEQUENCE: 39
atacatgcct cctcccctag g                                              21

<210> SEQ ID NO 40
<211> LENGTH: 20
<212> TYPE: DNA
<213> ORGANISM: Homo sapiens
```

```
<400> SEQUENCE: 40
cactttggct tgaggaccca                                              20

<210> SEQ ID NO 41
<211> LENGTH: 18
<212> TYPE: DNA
<213> ORGANISM: Homo sapiens

<400> SEQUENCE: 41
cagccccagc tcctttcc                                                18

<210> SEQ ID NO 42
<211> LENGTH: 17
<212> TYPE: DNA
<213> ORGANISM: Homo sapiens

<400> SEQUENCE: 42
tgggcccggt ttctcat                                                 17

<210> SEQ ID NO 43
<211> LENGTH: 20
<212> TYPE: DNA
<213> ORGANISM: Homo sapiens

<400> SEQUENCE: 43
ggggtacaat ggcgaggtct                                              20

<210> SEQ ID NO 44
<211> LENGTH: 30
<212> TYPE: DNA
<213> ORGANISM: Homo sapiens

<400> SEQUENCE: 44
agtctactcc aaacctaggt ctctatgtca                                   30

<210> SEQ ID NO 45
<211> LENGTH: 16
<212> TYPE: DNA
<213> ORGANISM: Homo sapiens

<400> SEQUENCE: 45
tgggacccag ccccag                                                  16

<210> SEQ ID NO 46
<211> LENGTH: 21
<212> TYPE: DNA
<213> ORGANISM: Homo sapiens

<400> SEQUENCE: 46
gcacacggat taggctgagt g                                            21

<210> SEQ ID NO 47
<211> LENGTH: 18
<212> TYPE: DNA
<213> ORGANISM: Homo sapiens

<400> SEQUENCE: 47
cctaccaccc ccaaccca                                                18

<210> SEQ ID NO 48
<211> LENGTH: 25
<212> TYPE: DNA
<213> ORGANISM: Homo sapiens
```

```
<400> SEQUENCE: 48
gagcagtact ccgactacag ctacc                                   25

<210> SEQ ID NO 49
<211> LENGTH: 15
<212> TYPE: DNA
<213> ORGANISM: Homo sapiens

<400> SEQUENCE: 49
tggcccccaa cacgg                                              15

<210> SEQ ID NO 50
<211> LENGTH: 16
<212> TYPE: DNA
<213> ORGANISM: Homo sapiens

<400> SEQUENCE: 50
tccccgcatc cacctg                                             16

<210> SEQ ID NO 51
<211> LENGTH: 20
<212> TYPE: DNA
<213> ORGANISM: Homo sapiens

<400> SEQUENCE: 51
aatgtgtttg caggtggcag                                         20

<210> SEQ ID NO 52
<211> LENGTH: 21
<212> TYPE: DNA
<213> ORGANISM: Homo sapiens

<400> SEQUENCE: 52
ggaggccaaa agtggttaaa c                                       21

<210> SEQ ID NO 53
<211> LENGTH: 20
<212> TYPE: DNA
<213> ORGANISM: Homo sapiens

<400> SEQUENCE: 53
tcatcctcgt cctccactgg                                         20

<210> SEQ ID NO 54
<211> LENGTH: 19
<212> TYPE: DNA
<213> ORGANISM: Homo sapiens

<400> SEQUENCE: 54
ggcacagcct tggtccatc                                          19

<210> SEQ ID NO 55
<211> LENGTH: 18
<212> TYPE: DNA
<213> ORGANISM: Homo sapiens

<400> SEQUENCE: 55
ttgccacgct gcttggag                                           18

<210> SEQ ID NO 56
<211> LENGTH: 21
<212> TYPE: DNA
<213> ORGANISM: Homo sapiens
```

```
<400> SEQUENCE: 56
gtcttggtga gacggtcagc c                                          21

<210> SEQ ID NO 57
<211> LENGTH: 17
<212> TYPE: DNA
<213> ORGANISM: Homo sapiens

<400> SEQUENCE: 57
gtggcgccgc tcaatct                                               17

<210> SEQ ID NO 58
<211> LENGTH: 24
<212> TYPE: DNA
<213> ORGANISM: Homo sapiens

<400> SEQUENCE: 58
caacggtgac tttgttatcc agaa                                       24

<210> SEQ ID NO 59
<211> LENGTH: 18
<212> TYPE: DNA
<213> ORGANISM: Homo sapiens

<400> SEQUENCE: 59
aagctgagcg aggtggga                                              18

<210> SEQ ID NO 60
<211> LENGTH: 24
<212> TYPE: DNA
<213> ORGANISM: Homo sapiens

<400> SEQUENCE: 60
gagagctatg agttgaaggt ggtg                                       24

<210> SEQ ID NO 61
<211> LENGTH: 23
<212> TYPE: DNA
<213> ORGANISM: Homo sapiens

<400> SEQUENCE: 61
ctggcatgtt ctccatcact gag                                        23

<210> SEQ ID NO 62
<211> LENGTH: 23
<212> TYPE: DNA
<213> ORGANISM: Homo sapiens

<400> SEQUENCE: 62
acaacgcacc tgtcttcact cag                                        23

<210> SEQ ID NO 63
<211> LENGTH: 22
<212> TYPE: DNA
<213> ORGANISM: Homo sapiens

<400> SEQUENCE: 63
agatggtgaa gaggccctta gc                                         22

<210> SEQ ID NO 64
<211> LENGTH: 19
<212> TYPE: DNA
<213> ORGANISM: Homo sapiens
```

```
<400> SEQUENCE: 64
gcaggtgatg tgcccttcc                                              19

<210> SEQ ID NO 65
<211> LENGTH: 22
<212> TYPE: DNA
<213> ORGANISM: Homo sapiens

<400> SEQUENCE: 65
ggagttagtg ctggagagtg gg                                          22

<210> SEQ ID NO 66
<211> LENGTH: 17
<212> TYPE: DNA
<213> ORGANISM: Homo sapiens

<400> SEQUENCE: 66
caagagtgcc cgtgccc                                                17

<210> SEQ ID NO 67
<211> LENGTH: 22
<212> TYPE: DNA
<213> ORGANISM: Homo sapiens

<400> SEQUENCE: 67
gtctcctctg ccacatcctc tg                                          22

<210> SEQ ID NO 68
<211> LENGTH: 26
<212> TYPE: DNA
<213> ORGANISM: Homo sapiens

<400> SEQUENCE: 68
ccctgatcta aaccatctct gttctc                                      26

<210> SEQ ID NO 69
<211> LENGTH: 21
<212> TYPE: DNA
<213> ORGANISM: Homo sapiens

<400> SEQUENCE: 69
ctgtccatgc gaagaagacg c                                           21

<210> SEQ ID NO 70
<211> LENGTH: 22
<212> TYPE: DNA
<213> ORGANISM: Homo sapiens

<400> SEQUENCE: 70
tgtcccatct ccaatagttg cc                                          22

<210> SEQ ID NO 71
<211> LENGTH: 28
<212> TYPE: DNA
<213> ORGANISM: Homo sapiens

<400> SEQUENCE: 71
caatacatag atgattcgtt taaggcct                                    28

<210> SEQ ID NO 72
<211> LENGTH: 17
<212> TYPE: DNA
<213> ORGANISM: Homo sapiens
```

<400> SEQUENCE: 72
atggtggtgg gccctgt                                              17

<210> SEQ ID NO 73
<211> LENGTH: 20
<212> TYPE: DNA
<213> ORGANISM: Homo sapiens

<400> SEQUENCE: 73
gacactgcat gaccagcagg                                           20

<210> SEQ ID NO 74
<211> LENGTH: 20
<212> TYPE: DNA
<213> ORGANISM: Homo sapiens

<400> SEQUENCE: 74
actgggctcc ttcccttgac                                           20

<210> SEQ ID NO 75
<211> LENGTH: 21
<212> TYPE: DNA
<213> ORGANISM: Homo sapiens

<400> SEQUENCE: 75
ccctgcttca gggctaaaat t                                         21

<210> SEQ ID NO 76
<211> LENGTH: 18
<212> TYPE: DNA
<213> ORGANISM: Homo sapiens

<400> SEQUENCE: 76
ccaaatggcc cattccag                                             18

<210> SEQ ID NO 77
<211> LENGTH: 22
<212> TYPE: DNA
<213> ORGANISM: Homo sapiens

<400> SEQUENCE: 77
gatggaaatg aggggagagg ac                                        22

<210> SEQ ID NO 78
<211> LENGTH: 17
<212> TYPE: DNA
<213> ORGANISM: Homo sapiens

<400> SEQUENCE: 78
acaccaaaac ggccccc                                              17

<210> SEQ ID NO 79
<211> LENGTH: 16
<212> TYPE: DNA
<213> ORGANISM: Homo sapiens

<400> SEQUENCE: 79
gtgtggctgc gggtgg                                               16

<210> SEQ ID NO 80
<211> LENGTH: 20
<212> TYPE: DNA
<213> ORGANISM: Homo sapiens -continued

```
<400> SEQUENCE: 80
ccgctccctc ctacagacct                                               20

<210> SEQ ID NO 81
<211> LENGTH: 19
<212> TYPE: DNA
<213> ORGANISM: Homo sapiens

<400> SEQUENCE: 81
ccgttttggt gttccggtc                                                19

<210> SEQ ID NO 82
<211> LENGTH: 19
<212> TYPE: DNA
<213> ORGANISM: Homo sapiens

<400> SEQUENCE: 82
tgcctgtgag ttcagcggt                                                19

<210> SEQ ID NO 83
<211> LENGTH: 15
<212> TYPE: DNA
<213> ORGANISM: Homo sapiens

<400> SEQUENCE: 83
atccctggcg ctgcg                                                    15

<210> SEQ ID NO 84
<211> LENGTH: 20
<212> TYPE: DNA
<213> ORGANISM: Homo sapiens

<400> SEQUENCE: 84
cccgattaat accagtgcgg                                               20

<210> SEQ ID NO 85
<211> LENGTH: 17
<212> TYPE: DNA
<213> ORGANISM: Homo sapiens

<400> SEQUENCE: 85
tcccaaccca ggcatcc                                                  17

<210> SEQ ID NO 86
<211> LENGTH: 19
<212> TYPE: DNA
<213> ORGANISM: Homo sapiens

<400> SEQUENCE: 86
aaaggcgctg tcctctcca                                                19

<210> SEQ ID NO 87
<211> LENGTH: 20
<212> TYPE: DNA
<213> ORGANISM: Homo sapiens

<400> SEQUENCE: 87
cttagttctg gccctgcct                                                20
```

-continued

<210> SEQ ID NO 88
<211> LENGTH: 22
<212> TYPE: DNA
<213> ORGANISM: Homo sapiens

<400> SEQUENCE: 88
ctacaaacat ttcctgagcc cc                                                22

<210> SEQ ID NO 89
<211> LENGTH: 19
<212> TYPE: DNA
<213> ORGANISM: Homo sapiens

<400> SEQUENCE: 89
gccagaattt ccggctcaa                                                   19

<210> SEQ ID NO 90
<211> LENGTH: 22
<212> TYPE: DNA
<213> ORGANISM: Homo sapiens

<400> SEQUENCE: 90
caacccttcc taaacctgag gc                                                22

<210> SEQ ID NO 91
<211> LENGTH: 20
<212> TYPE: DNA
<213> ORGANISM: Homo sapiens

<400> SEQUENCE: 91
tcctcaccct tcactgtggg                                                  20

<210> SEQ ID NO 92
<211> LENGTH: 20
<212> TYPE: DNA
<213> ORGANISM: Homo sapiens

<400> SEQUENCE: 92
ccttgctgct ttcggagaga                                                  20

<210> SEQ ID NO 93
<211> LENGTH: 20
<212> TYPE: DNA
<213> ORGANISM: Homo sapiens

<400> SEQUENCE: 93
ggagaccgag gctgagacct                                                  20

<210> SEQ ID NO 94
<211> LENGTH: 20
<212> TYPE: DNA
<213> ORGANISM: Homo sapiens

<400> SEQUENCE: 94
agctgacgcg ttctgaggat                                                  20

METHODS FOR DETERMINING THE RISK OF DEVELOPING ASTHMA CHARACTERIZED BY BRONCHIAL HYPERRESPONSIVENESS

This application is a nonprovisional application of U.S. Provisional Application No. 60/305,649, filed Jul. 16, 2001.

The present invention relates to the use of an asthma-associated gene, designated AAGA, the protein molecule encoded by AAGA and related molecules in diagnostic and prognostic screening of patient populations, to polymorphisms in AAGA, and to the use of the protein encoded by AAGA or a variant thereof as a therapeutic target.

Asthma is a very common lung disease with the following characteristics: airways obstruction—this is usually reversible but often progressive chronic bronchial inflammation—a condition characterised by inflammatory cell infiltration and activation, release of biochemical mediators and structural changes (airway remodelling) bronchial hyperresponsiveness (BHR)—an exaggerated bronchoconstrictor response to a variety of immunologic, biochemical and physical stimuli.

Asthma is characterised clinically by chronic, intermittent airway obstruction with wheezing, coughing and breathlessness. Although asthma is typically associated with an obstructive impairment that is reversible, neither this finding nor any other single test or measure is adequate to diagnose asthma [Guidelines for the diagnosis and development of asthma, 1997, NIH Publication No. 97-4051]. Many diseases are associated with this pattern of abnormality. The patient's pattern of symptoms (along with other information from the patient's medical history) and exclusion of other possible diagnoses also are needed to establish a diagnosis of asthma. Clinical judgement is needed in conducting the assessment for asthma. Patients with asthma are heterogeneous and present signs and symptoms that vary widely from patient to patient as well as within each patient over time.

Many hypotheses have been advanced to explain the pathophysiology of asthma, including problems with airway smooth muscle, the role of inflammation, nervous innervation of the airways and mechanisms related to mediators. Although all of these factors may be important, it is unclear which are the primary (i.e. causative) defects and which are the secondary defects. It is generally agreed, however, that both the environment and genetics are important. Given the multifactorial nature of asthma, one approach to identifying the fundamental mechanisms is to discover asthma susceptibility genes that predispose individuals to develop asthma.

One method which can be used to identify asthma susceptibility genes is positional cloning. In this method, susceptibility genes are localised to a specific region of a human chromosome by using DNA markers to track the inheritance of the genes through families. DNA markers are fragments of DNA with a defined physical location on a chromosome, whose inheritance can be monitored. The closer a DNA marker is to a susceptibility gene, the greater the probability that the marker and the susceptibility gene will be passed together from parent to child. This phenomenon is called genetic linkage. Once linkage to a specific chromosomal region has been obtained, the size of the region is narrowed down using a combination of physical and genetic mapping until the region is small enough to be sequenced and the susceptibility gene can be identified. After identification of the susceptibility gene, any polymorphisms in this gene can be determined and an analysis performed to see whether these mutations occur with greater prevalence in asthmatics compared to non-asthmatics. The major advantages of positional cloning are that it is possible to identify novel genes even though the underlying factors causing the disease are unknown, and the genes identified are of direct pathological relevance (i.e. primary causative defects) because they make carriers directly susceptible to developing the disease.

In recent years a number of academic research groups have provided evidence for the presence of genes important in the regulation of asthmatic and allergic responses on human chromosome 5. In particular, evidence for the presence of susceptibility genes for BHR and elevated serum IgE levels on chromosome 5 in subregion 5q31–5q33 [Meyers et al., Genomics 23: 464–470; Postma et al., N. Eng. J. Med. 333:894–900; and Bleecker et al., Clin. Exp. Allergy 25:84–88] was obtained from genetic linkage analysis of 92 Dutch asthma families. Strong evidence for genetic linkage between marker D5S436, total serum IgE levels [Meyers et al., Genomics 23: 464–470; Postma et al., N. Eng. J. Med. 333:894–900; and Bleecker et al., Clin. Exp. Allergy 25:84–88] and BHR [Postma et al., N. Eng. J. Med. 333: 894–900; and Bleecker et al., Clin. Exp. Allergy 25:84–88] was found in the Dutch families.

No asthma susceptibility gene has yet been identified, so there is a need in the art for the identification of such genes. Identification of asthma susceptibility genes would provide a fundamental understanding of the disease process from which a number of clinically important applications would arise. Susceptibility genes identified may lead to the development of therapeutics (small molecule drugs, antisense molecules, antibody molecules) directly targeted to the gene or protein product of the gene, or may target the biochemical pathway of which the protein product is a part at an upstream or downstream location if the development of such drugs is easier than directly targeting the gene or its protein product.

Polynucleotide sequences comprising the gene, sequence variants thereof and protein products thereof may be used to develop a clinical diagnostic test for asthma and for the identification of individuals at high risk for the development of asthma. The results of such tests may also have prognostic value and may be used to predict patients who respond to and those who do not respond to drug therapy. Finally, information about the DNA sequences of asthma susceptibility genes and the amino acid sequences encoded by these genes facilitates large scale production of proteins by recombinant techniques and identification of the tissues/cells naturally producing the proteins. Such sequence information also permits the preparation of antibody substances or other novel binding molecules specifically reactive with the proteins encoded by the susceptibility genes that may be used in modulating the natural ligand/antiligand binding reactions in which the proteins may be involved and for diagnostic purposes.

Terms used herein have the following meanings:

"Isolated" refers to material removed from its original environment.

"Hybridization" or "hybridizes" refers to any process by which a strand of a polynucleotide binds with a complementary strand through base pairing.

"Stringent conditions" refer to experimental conditions which allow up to 20% base pair mismatches, typically two 15 minute washes in 0.1×SSC (15 mM NaCl, 1.5 mM sodium citrate, pH 7.0) at 65° C.

"Homology" or "homologous" refers to a degree of similarity between nucleotide or amino acid sequences, which may be partial or, when sequences are identical, complete.

"Expression vector" refers to a linear or circular DNA molecule which comprises a segment encoding a polypeptide of interest operably linked to additional segments which provide for its transcription.

"Antisense" refers to selective inhibition of protein synthesis through hybridisation of an oligo- or polynucleotide to its complementary sequence in messenger RNA (mRNA) of the target protein. The antisense concept was first proposed by Zamecnik and Stephenson (Proc. Natl. Acad. Sci. USA 75:280–284; Proc. Natl. Acad. Sci. USA 75:285–288) and has subsequently found broad application both as an experimental tool and as a means of generating putative therapeutic molecules (Alama, A., Pharmacol. Res. 36:171–178; Dean, N. M., Biochem. Soc. Trans. 24:623–629; Bennet, C. F., J. Pharmacol. Exp. Ther. 280:988–1000; Crooke, S. T., Antisense Research and Applications, Springer).

It has now been found by genetic linkage analysis and bioinformatics analysis that AAGA, a gene on chromosome 5 comprising a nucleotide sequence encoding a polypeptide having the amino acid sequence of SEQ ID NO: 7 or SEQ ID NO: 8, which nucleotide sequence has 100% homology with mRNA sequences and ESTs corresponding to the protocadherin-42 gene, is associated with bronchial hyperresponsiveness. Protocadherin-42 is a member of the cadherin superfamily. Proteins of this superfamily are involved in cell-cell (intercellular) adhesion, which plays an important role in a wide range of events in vivo and is crucial for the maintenance of tissue integrity—see M. Takeichi, Annu. Rev. Biochem (1990), 58, 237–52. AAGA has been found to be expressed at a high level in human bronchial epithelial cells. It has also been found that polymorphisms in AAGA occur more prevalently in asthmatic patients than they do in non-asthmatics.

Accordingly, in one aspect, the present invention provides a method for determining whether a subject has, or is at risk of developing, a disease characterised by bronchial hyperresponsiveness, comprising determining, in a sample of cells from the subject, (i) the level of expression of a polynucleotide (A) comprising the nucleotide sequence SEQ ID NO:1 or SEQ ID NO:2 or SEQ ID NO:3 or SEQ ID NO: 4 or SEQ ID NO: 5 or SEQ ID NO: 6 or a sequence which hybridises thereto under stringent conditions, polynucleotide (A) being hereinafter referred to alternatively as the AAGA gene, or the level of expression of a polypeptide (B) comprising the amino acid sequence SEQ ID NO: 7 or SEQ ID NO: 8 or a functionally equivalent variant thereof, or the level of a bioactivity of said polypeptide (B) and comparing the level of expression of (A) or (B) or the level of bioactivity of (B) with the respective level of expression of (A) or (B) or bioactivity in a healthy subject, or (ii) the presence of a variant of said polynucleotide (A) or said polypeptide (B) associated with bronchial hyperresponsiveness.

The term "variant" as used herein means, in relation to amino acid sequences, an amino acid sequence that is altered by one or more amino acids. The changes may involve amino acid substitution, deletion or insertion. In relation to nucleotide sequences, the term "variant" as used herein means a nucleotide sequence that is altered by one or more nucleotides; the changes may involve nucleotide substitution, deletion or insertion. A preferred functionally equivalent variant of the amino acid sequence SEQ ID NO:7 or SEQ ID NO:8 is one having at least 80%, more preferably at least 90%, and especially more than 95% amino acid sequence identity to SEQ ID NO:7 or SEQ ID NO:8. In such preferred functionally equivalent variants, the regions of SEQ ID NO:7 or SEQ ID NO:8 corresponding to the extracellular domain are usually substantially conserved.

By an amino acid sequence having x % identity to a reference sequence such as SEQ ID NO:7 or SEQ ID NO:8, is meant a sequence which is identical to the reference sequence except that it may include up to 100-x amino acid alterations per each 100 amino acids of the reference sequence. For example, in a subject amino acid sequence having at least 80% identity to a reference sequence, up to 20% of the amino acid residues in the reference sequence may be substituted, deleted or inserted with another amino acid residue. Percentage identity between amino acid sequences can be determined conventionally using known computer programs, for example the FASTDB program based on the algorithm of Brutlag et al (Comp.App.Biosci. (1990) 6:237–245).

The level of expression of a polynucleotide (A) as hereinbefore defined or a polypeptide (B) as hereinbefore defined may be determined, for example, by Nothern blot analysis, reverse transcription-polymerase chain reaction (RT-PCR), in situ hybridization, immunoprecipitation, Western blot hybridization or immunohistochemistry. The level of (A), e.g. as mRNA, or the polypeptide (B), measured by one of the above techniques, in cells from the subject, may be compared with the level of (A) or (B) respectively in a healthy subject. An abnormal level of polynucleotide (A) or polypeptide (B) is likely to be indicative of aberrant AAGA activity associated with bronchial hyperresponsiveness.

The level of a bioactivity of the polypeptide (B) can be measured, for example, by measuring calcium-dependent cell-cell adhesion, for instance by promoting homotypic $Ca^{2+}$ dependent aggregation and adhesion in L-cells, e.g. as described by Sano et al, EMBO J. 12: 2249–2256. Comparison of the measured activity in cells from the subject with the activity measured in cells from a healthy subject indicates whether a subject has abnormal AAGA activity associated with bronchial hyperresponsiveness.

A variant of polynucleotide (A) associated with bronchial hyperresponsiveness may be a variant having an alteration which alters the amino acid sequence in the encoded polypeptide or which alters the expression level of the encoded polypeptide, the stability of a transcript or the way in which a transcript is processed. Such alterations may involve at least one of the following: (i) a deletion of one or more nucleotides from polynucleotide (A), (ii) an addition of one or more nucleotides to polynucleotide (A), (iii) a substitution of one or more nucleotides of polynucleotide (A), (iv) a gross chromosomal rearrangement of polynucleotide (A), (v) a gross alteration in the level of a messenger RNA transcript of polynucleotide (A), (vi) aberrant modification of polynucleotide (A), such as of the methylation pattern of the genomic DNA, (vii) the presence of a non-wild type splicing pattern of a messenger RNA transcript of polynucleotide (A), (viii) a non-wild type level of polypeptide (B), (ix) allelic loss of polynucleotide (A), and/or (x) inappropriate post-translational modification of polypeptide (B). Various assay techniques may be used to detect alterations in an AAGA gene (polynucleotide (A). These methods include, but are not limited to, methods involving sequence analysis, Southern blot hybridization, conformation sensitive gel electrophoresis (CSGE), restriction enzyme site mapping, and methods involving detection of the absence of nucleotide pairing between the nucleic acid to be analyzed and a probe.

Accordingly, in one embodiment, the variant of polynucleotide (A), i.e. genetic abornmality, associated with bronchial hyperresponsiveness in a subject is detected by incubating a DNA sample from the subject with a polynucleotide probe comprising at least 5, e.g. at least 15 contiguous nucleotides of polynucleotide (A) as hereinbefore defined, under conditions where the probe hybridises to complementary polynucleotide sequence, to produce a first reaction product, and comparing the first reaction product with a control reaction product obtained from the probe and DNA from a healthy subject. If there is a difference between the first reaction product and the control reaction product which is correlated with bronchial hyperresponsiveness, e.g. in asthmatics, the difference indicates a predisposition to developing a disease characterised by bronchial hyerresponsiveness. The probe is generally a synthetic oligonucleotide having 15 to 50 nucleotides, and may be labelled, e.g. with a fluorophore or radioactive nucleotide, to provide a detectable signal.

AAGA mutations that are particularly likely to cause or contribute to the development of asthma or other inflammatory or obstructive airways diseases characterised by BHR are those mutations that negatively impact normal (wild-type) functioning of AAGA, in particular the extracellular domain which is involved in homotypic association and therefore cell-cell adhesion and the intracellular domain which interacts with structural proteins or signalling molecules. Examples of such mutations include: i) mutations that affect the level of transcripts produced; ii) missense mutations occurring within the intracellular, transmembrane or extracellular domain; and mutations which affect the way in which the transcript is processed.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions in genes, e.g, AAGA genes, can be identified, by determining the nucleotide sequence of genes in populations of individuals. If a polymorphic region, e.g., SNP or a haplotype, i.e. a combination of SNPs, is identified, then the link with a specific disease can be determined by studying specific populations of individuals, e.g, individuals which developed a specific disease, such as asthma. A polymorphic region can be located in any region of a gene, e.g., exons, in coding or non coding regions of exons, introns, and promoter regions.

It has been found that AAGA genes comprise polymorphic regions, specific alleles of which are associated with bronchial hyperresponsiveness, particularly in asthmatic patients. Thus, determining the presence of a variant of a polynucleotide (A) as hereinbefore defined may comprise determining the identity of an allele or allelic variant of a polymorphism of a polynucleotide (A) in a subject, thereby to determine whether the subject has a specific allelic variant of a polymorphism which is associated with bronchial hyperresponsiveness.

Numerous SNPs in SEQ ID NO: 1 identified in DNA samples from asthmatic patients are shown in Example 3. Of these, the polymorphisms at positions 6377 (a change from C to T) and 7390 (a change from G to C) of SEQ ID NO: 1 have been shown to be associated with bronchial hyper-responsiveness. Accordingly, in a preferred embodiment, determining the presence of a variant of polynucleotide (A) as hereinbefore described comprises determining, in a sample of cells from the subject, the identity of the base at one or both of the positions corresponding to positions 6377 and 7390 in SEQ ID NO: 1. The presence of T at the position corresponding to said position 6377 and/or C at the position corresponding to said position 7390 indicates a variant of polynucleotide (A) associated with bronchial hyperresponsiveness. When it is desired to determine the presence of a haplotype, i.e. a combination of SNPs, the identity of the base at positions corresponding to both positions 6377 and 7390 may be determined, or the identity of the base at one or both of these positions and the identity of the base at one or more of the positions corresponding to positions 589, 1001, 1060, 2033, 2193, 2561, 5667, 5804 and 7531 in SEQ ID NO: 1 and positions 1212, 1216, 1964 and 2330 in SEQ ID NO: 2 may be determined. In a specifically preferred embodiment, a nucleic acid comprising SEQ ID NO: 1, or a portion thereof comprising nucleotide 6377 and/or nucleotide 7390, is isolated from the cell sample and sequenced.

In an exemplary embodiment, DNA of a sample cell from a subject is rendered accessible for hybridization and is contacted with a nucleic acid probe including a region of nucleotide sequence which is capable of hybridizing to a sense or antisense sequence of an AAGA gene (polynucleotide (A)) or naturally occurring mutants thereof, e.g. a polymorphic region of the gene such as a region including position 6377 and/or position 7390 of SEQ ID NO: 1, or 5' or 3' flanking sequences naturally associated with AAGA genes or naturally occurring mutants thereof and hybridization of the probe to the sample DNA is detected. Such techniques can be used to detect alterations or allelic variants at either the genomic or mRNA level, including deletions, substitutions, etc., as well as to determine mRNA transcript levels.

Another method of identifying an allele or allelic variant of a polymorphic region is allele specific hybridization using probes overlapping the mutation or polymorphic site and having about from 5 to 30, e.g. 5, 10, 20, 25, or 30 nucleotides. In a preferred embodiment, several probes capable of hybridizing specifically to allelic variants, such as single nucleotide polymorphisms, are attached to a solid phase support, e.g., a "chip". Oligonucleotides can be bound to a solid support by a variety of processes, including lithography. For example a chip can hold up to about 250,000 oligonucleotides. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes in a DNA sample from a patient can be identified in a simple hybridization experiment.

Accordingly, the invention in another aspect provides an allele-specific oligonucleotide probe capable of detecting a polymorphism in polynucleotide (A) as hereinbefore described at one or more of positions 6377 and 7390 of SEQ ID NO: 1. The allele-specific probe generally has about 15–50 nucleotides, more usually about 15–30 nucleotides, and overlaps said position 6377 or 7390. Conveniently a central position of the probe aligns with said position 6377 or 7390. The nucleotide sequence of such a probe is generally 100% complementary to the corresponding sequence in the polymorphic region of the polynucleotide (A). The probe may be labelled, e.g. conventionally, e.g. with a fluorophore or radioactive label, to provide a detectable signal.

In certain embodiments, detection of the alteration comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) Science 241:1077–1080; and Nakazawa et al. (1994) PNAS 91:360–364), the latter of which can be particularly useful for detecting point mutations in the AAGA gene (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an AAGA gene under conditions such that hybridization and amplification of the AAGA gene (if present) occurs, and (iv) detecting the presence or absence of an amplification product, or detecting the size of the amplification product and comparing the length to a control sample. It is anticipated that PCR, LCR or any other amplification procedure (e.g. self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), or Q-Beta Replicase (Lizardi, P. M. et al., 1988, Bio/Technology 6:1197)), may be used as a preliminary step to increase the amount of sample on which can be performed any of the techniques for detecting mutations described herein.

A preferred method of determining the presence of a variant of a polynucleotide (A) as hereinbefore defined, where the variant comprises a single nucleotide polymorphism, comprises determining the allelic variant by sequencing a DNA sample from the subject. In another method of identifying an allelic variant of a polymorphism, DNA fragments from a cell sample are amplified by PCR in the presence of an allele-specific primer capable of detecting a polymorphism in polynucleotide (A), particularly at one or more of positions 6377 and 7390 of SEQ ID NO 1. Numerous SNPs identified in DNA samples from asthmatic patients are shown in Example 2. Of these, the polymorphisms at positions 6377 and 7390 in SEQ ID NO: 1 have been shown in certain populations to be associated with bronchial hyperresponsiveness.

The invention also provides an allele-specific primer, for example for use in polymorphism-detecting procedures including an amplification step, capable of detecting a polymorphism in polynucleotide (A) as hereinbefore defined at one or more of positions 6377 and 7390 in SEQ ID NO: 1. This primer generally has about 15 to 50 nucleotides, more usually about 15–30 nucleotides. The nucleotide sequence of the primer corresponds with that of the allele to be detected, although a partially corresponding sequence with about 5 to 10 of the nucleotides at the 3' end of the primer corresponding with those of the allele to be detected may be used.

The primer may be labelled, e.g. with a fluorophore or radioactive label, to assist detection thereof.

The invention further provides a diagnostic or prognostic kit comprising an allele-specific oligonucleotide probe as hereinbefore described or an allele-specific primer as hereinbefore described, optionally together with other reagents such as labelling reagents (to incorporate a detectable label into a hybridised product), buffers and DNA polymerases such as Taq polymerase.

Accordingly, in another aspect the invention provides an isolated polynucleotide which is a variant of polynucleotide (A) as hereinbefore defined associated with bronchial hyperresponsiveness, particularly a variant of polynucleotide (A) having a specific allelic variant of a single nucleotide polymorphism associated with bronchial hyperresponsiveness, such as a single nucleotide polymorphism at position 6377 and/or position 7390 of SEQ ID No: 1, especially T at said position 6377 and/or C at said position 7390. Correspondingly, in a further aspect the invention provides an isolated mutant polypeptide associated with bronchial hyperresponsiveness which is encoded by the polynucleotide variant of polynucleotide (A) associated with bronchial hyperresponsiveness as hereinbefore described, or an isolated polypeptide which is a variant of polypeptide (B) as hereinbefore defined associated with bronchial hyperresponsiveness.

Information obtained using the diagnostic assays described herein (alone or in conjunction with information on another genetic defect, which contributes to the same disease) is useful for prognosing, diagnosing or confirming that a symptomatic subject has a genetic defect (e.g. in an AAGA gene or in a gene that regulates the expression of an AAGA gene), which causes or contributes to the particular disease or disorder. Alternatively, the information (alone or in conjunction with information on another genetic defect, which contributes to the same disease) can be used prognostically for predicting whether a non-symptomatic subject is likely to develop a disease or condition, which is caused by or contributed to by an abnormal AAGA activity or protein level in a subject. In particular, the assays permit one to ascertain an individual's predilection to develop bronchial hyperresponsiveness associated with a mutation in or associated with AAGA, where the mutation is a polymorphism such as a single nucleotide polymorphism (SNP). Based on the prognostic information, a doctor can recommend a regimen e.g. a therapeutic protocol useful for preventing or delaying onset of asthma in the individual.

Knowledge of the particular alteration or alterations, resulting in defective or deficient AAGA genes or proteins in an individual (the AAGA genetic profile), alone or in conjunction with information on other genetic defects contributing to the same disease (the genetic profile of the particular disease) allows a customization of the therapy for a particular disease to the individual's genetic profile, the goal of "pharmacogenomics". For example, subjects having a specific allele of an AAGA gene may or may not exhibit symptoms of a particular disease or be predisposed of developing symptoms of a particular disease. Further, if those subjects are symptomatic, they may or may not respond to a certain drug, e.g., a specific AAGA therapeutic, but may respond to another. Thus, generation of an AAGA genetic profile, (e.g., categorization of alterations in AAGA genes which are associated with the development of asthma), from a population of subjects, who are symptomatic for a disease or condition that is caused by or contributed to by a defective and/or deficient AAGA gene and/or protein (an AAGA genetic population profile) and comparison of an individual's AAGA profile to the population profile, permits the selection or design of drugs that are expected to be safe and efficacious for a particular patient or patient population (i.e., a group of patients having the same genetic alteration).

Accordingly, in another aspect, the invention provides a method for pharmacogenomically selecting a therapy to administer to an individual having asthma, comprising determining an AAGA genetic profile of an individual and comparing the individual's AAGA genetic profile to an AAGA genetic population profile, thereby to select a therapy for administration to the individual.

For example, an AAGA population profile can be performed by determining the AAGA profile, e.g., the identity of AAGA genes, in a patient population having a disease which is caused by or contributed to by a defective or deficient AAGA gene. Optionally, the AAGA population profile can further include information relating to the response of the population to an AAGA therapeutic, using any of a variety of methods, including, monitoring: 1) the severity of symptoms associated with the AAGA related disease, 2) AAGA gene expression level, 3) AAGA mRNA level, and/or 4) AAGA protein level. and (iii) dividing or categorizing the population based on the particular genetic alteration or alterations present in its AAGA gene or an AAGA pathway gene. The AAGA genetic population profile can also, optionally, indicate those particular alterations in which the patient was either responsive or non-responsive to a particular therapeutic. This information or population profile is then useful for predicting which individuals should respond to particular drugs, based on their individual AAGA profile.

In a preferred embodiment, the AAGA profile is a transcriptional or expression level profile and step (i) is comprised of determining the expression level of AAGA proteins, alone or in conjunction with the expression level of other genes, known to contribute to the same disease.

The AAGA profile can be measured in many patients at various stages of the disease. Pharmacogenomic studies can also be performed using transgenic animals. For example, transgenic mice which contain a specific allelic variant of an AAGA gene can be created, e.g, by replacing their wild-type AAGA gene with an allele of the human AAGA gene. The response of these mice to specific AAGA therapeutics can then be determined.

The treatment of an individual with an AAGA therapeutic can be monitored by determining AAGA characteristics, such as AAGA protein level or activity, AAGA mRNA level, and/or AAGA transcriptional level. These measurements will indicate whether the treatment is effective or whether it should be adjusted or optimized. Thus, AAGA can be used as a marker for the efficacy of a drug during clinical trials.

In a preferred embodiment, the present invention provides a method for monitoring the effectiveness of treatment of a subject with a pharmaceutical (e.g., an agonist, antagonist, peptidomimetic, protein, peptide, nucleic acid, small molecule, or other drug candidate identified by the screening assays described herein) comprising the steps of determining the level of expression of a polynucleotide (A), e.g. as mRNA or genomic DNA, or a polypeptide (B), or the level of an activity of said polynucleotide (A) or polypeptide (B) in a preadministration DNA sample from the subject and in a post-administration DNA sample from the subject, comparing the respective level of expression or activity in the pre-administration sample and the post administration sample and, if required, altering the administration of the pharmaceutical to the subject accordingly. For example, increased administration of the agent may be desirable to increase the expression or activity of AAGA to higher levels than detected, i.e., to increase the effectiveness of the agent. Alternatively, decreased administration of the agent may be desirable to decrease expression or activity of AAGA to lower levels than detected, i.e., to decrease the effectiveness of the agent.

Cells of a subject may also be obtained before and after administration of an AAGA therapeutic to detect the level of expression of genes other than AAGA, to verify that the AAGA therapeutic does not cause a deleterious increase or decrease in the expression of such genes. This can be done, e.g., by using the method of transcriptional profiling. Thus, mRNA from cells exposed in vivo to an AAGA therapeutic and mRNA from the same type of cells that were not exposed to the AAGA therapeutic could be reverse transcribed and hybridized to a chip containing DNA from numerous genes, to compare thereby the expression of genes in cells treated and not treated with an AAGA-therapeutic. If, for example an AAGA therapeutic turns on the expression of a proto-oncogene in an individual, use of this particular AAGA therapeutic may be undesirable.

An individual's AAGA genetic profile or the genetic profile of asthma can enable: 1) more effective prescription of a drug that will address the molecular basis of asthma; and 2) better determination of the appropriate dosage of a particular drug. The ability to target populations expected to show the highest clinical benefit, based on the AAGA or asthma genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of AAGA as a marker is useful for optimizing effective dose).

In another aspect, the invention provides a method of treating a disease characterised by bronchial hyperresponsiveness which comprises administering to a subject in need thereof an effective amount of a polynucleotide (A) as hereinbefore described, or a polypeptide (B) as hereinbefore described, or an antibody (C) which is immunoreactive with said polypeptide (B) or a variant thereof associated with the disease, or an antisense oligonucleotide (D) comprising a nucleotide sequence complementary to that of said polynucelotide (A) or a variant thereof associated with the disease.

The polynucleotide (A) may be cDNA comprising the nucleotide sequence of SEQ ID NO:4 or SEQ ID NO:5 or SEQ ID NO:6, a genomic DNA comprising the nucleotide sequence of SEQ ID NO:1 or SEQ ID NO:2 or SEQ ID NO:3 or a DNA comprising a nucleotide sequence which hybridises to SEQ ID NO:1 or SEQ ID NO:2 or SEQ ID NO:3 or SEQ ID NO:4 or SEQ ID NO:5 or SEQ ID NO:6 under stringent conditions.

In another aspect of the invention, the polynucleotide (A) comprises a portion having at least 20, e.g, at least 50, e.g. at least 100, e.g. at least 200, contiguous bases from SEQ ID NO:1 or SEQ ID NO:2 or SEQ ID NO:3 or SEQ ID NO:4 or SEQ ID NO:5 or SEQ ID NO:6. In a further aspect, the polynucleotide (A) comprises a nucleotide sequence encoding at least 10, e.g. at least 50, e.g. at least 100, e.g. at least 200, contiguous amino acids from SEQ ID NO:7 or SEQ ID NO:8.

The polynucleotide (A) may be isolated by bioinformatics analysis of DNA sequences from the subregion 5q31–5q33 on chromosome 5 determined by sequencing of yeast artificial chromosomes (YACs), bacterial artificial chromosomes (BACs) and/or P1 artificial chromosomes (PACs) to identify genes within that subregion, searching for a sequence having greater than 95% identity to the predicted exon for a selected gene and isolating cDNA from a human lung cDNA library by PCR using primers designed using that sequence.

The polynucleotide (A), for example having the sequence SEQ ID NO:1 or SEQ ID NO:2 or SEQ ID NO:3 or SEQ ID NO:4 or SEQ ID NO:5 or SEQ ID NO:6, may be prepared from the nucleotides which it comprises by chemical synthesis, e.g. automated solid phase synthesis using known procedures and apparatus.

In another aspect of the invention, the polypeptide (B) comprises a portion having at least 10, e.g. at least 50, e.g.

at least 100, e.g. at least 200 contiguous amino acids from SEQ ID NO:7, or SEQ ID NO:8.

The polypeptide (B) or mutant polypeptide as hereinbefore described may be produced by cloning a polynucleotide sequence or variant thereof as hereinbefore described into an expression vector containing a promoter and other appropriate regulating elements for transcription, transferring into prokaryotic or eukaryotic host cells such as bacterial, plant, insect, yeast, animal or human cells, and culturing the host cells containing the recombinant expression vector under suitable conditions. Techniques for such recombinant expression of polypeptides are well known and are described, for example, in J. Sambrook et al, Molecular Cloning, second edition, Cold Spring Harbor Press, 1990.

The polypeptide (B) or mutant polypeptide as hereinbefore described may be expressed as a recombinant fusion protein with one or more heterologous polypeptides, for example to facilitate purification. For example, it may be expressed as a recombinant fusion protein with a heterologous polypeptide such as a polyhistidine containing a cleavage site located between the polynucleotide sequence of the invention and the heterologous polypeptide sequence, so that the polypeptide comprising the amino acid sequence of SEQ ID NO:7 or SEQ ID NO:8, or variant thereof associated with bronchial hyperresponsiveness, may be cleaved and purified away from the heterologous moiety using well known techniques.

The polypeptide (B) or mutant polypeptide as hereinbefore described may also be synthesised, in whole or in part, from the amino acids which it comprises using well known chemical methods, for example automated solid phase techniques.

The polypeptide (B) or mutant polypeptide as hereinbefore described may be purified by well known standard procedures.

The antibody (C) may be a polyclonal or monoclonal antibody. Such antibodies may be prepared using conventional procedures. Methods for the production of polyclonal antibodies against purified antigen are well established (cf. Cooper and Paterson in Current Protocols in Molecular Biology, Ausubel et al. Eds., John Wiley and Sons Inc., Chapter 11). Typically, a host animal, such as a rabbit, or a mouse, is immunised with a purified polypeptide of the invention, or immunogenic portion thereof, as antigen and, following an appropriate time interval, the host serum is collected and tested for antibodies specific against the polypeptide. Methods for the production of monoclonal antibodies against purified antigen are well established (cf. Chapter 11, Current Protocols in Molecular Biology, Ausubel et al. Eds., John Wiley and Sons Inc.). For the production of a polyclonal antibody, the serum can be treated with saturated ammonium sulphate or DEAE Sephadex. For the production of a monoclonal antibody, the spleen or lymphocytes of the immunised animal are removed and immortalised or used to produce hybridomas by known methods. Antibodies secreted by the immortalised cells are screened to determine the clones which secrete antibodies of the desired specificity, for example using Western blot analysis. Humanised antibodies can be prepared by conventional procedures.

The antisense oligonucleotide (D) comprises a nucleotide sequence complementary to that of the mRNA of AAGA, in particular a nucleotide sequence complementary to SEQ ID NO:1 or SEQ ID NO:2 or SEQ ID NO:3 or SEQ ID NO:4 or SEQ ID NO:5 or SEQ ID NO:6, or complementary to that of a polynucleotide encoding a variant of a polypeptide (B) having a polymorphism correlated with the disease, e.g. asthma, in particular a nucleotide sequence complementary to such a polymorphic variant of SEQ ID NO:1 or SEQ ID NO:2 or SEQ ID NO:3 or SEQ ID NO:4 or SEQ ID NO:5 or SEQ ID NO:6. The antisense oligonucleotide may be DNA, an analogue of DNA such as a phosphorothioate or methylphosphonate analogue of DNA, RNA, an analogue of RNA, or a peptide nucleic acid (PNA). The antisense oligonucleotides may be synthesised by conventional methods, for example using automated solid phase techniques.

The role of the polypeptide (B) in asthma and other obstructive or inflammatory airways diseases characterised by bronchial hyperresponsiveness can be determined using conventional allergen driven animal models for bronchial hyperresponsiveness, e.g. the ovalbumin-induced BHR mouse model (Tsuyuki et al, J. Clin. Invest. 96:2924–2931) or the guinea pig model hereinafter described.

Polynucleotides, polypeptides, antibodies, or antisense oligonucleotides as hereinbefore described, hereinafter alternatively referred to collectively as agents of the invention, may be used in the treatment (prophylactic or symptomatic) of inflammatory or obstructive airways diseases. For example, a polypeptide (B) may be used to treat a mammal, particularly a human, deficient in or otherwise in need of that polypeptide; a polynucleotide (A) may be used in gene therapy where it is desired to increase AAGA activity, for instance where a subject has a mutated or missing AAGA gene; an antisense oligonucleotide (D) may be used to inhibit AAGA activity or activity of variants of the AAGA gene having a polymorphism correlated with a disease, e.g. asthma, where this is desired; and an antibody (C) may be used to inhibit ligand/antiligand binding activities of AAGA polypeptides.

"Gene therapy" refers to an approach to the treatment of human disease based upon the transfer of genetic material into somatic cells of an individual. Gene transfer can be achieved directly in vivo by administartion of gene-bearing viral or non-viral vectors into blood or tissues, or indirectly ex vivo through the introduction of genetic material into cells manipulated in the laboratory followed by delivery of the gene-containing cells back to the individual. By altering the genetic material within a cell, gene therapy may correct underlying disease pathophysiology. Suitable vectors, and procedures, for gene delivery to specific tissues and organ systems in animals are described in Dracopoli, N.C. et al., Current Protocols in Human Genetics. John Wiley and Sons Inc., Chapters 12 and 13 respectively. In relation to a polynucleotide (A) as hereinbefore described, gene therapy may involve delivery of a viral or non-viral gene therapy vector containing an expression cassette of the AAGA gene under suitable control elements to the lungs of diseased individuals (eg. asthmatics) so that the underlying disease pathophysiology is corrected or ameliorated.

The effectiveness of an agent of the invention in inhibiting or reversing airways hyperreactivity may be demonstrated in a guinea pig test model. The acute injection of pre-formed immune complex renders guinea pigs hyperreactive to histamine. Doses of histamine which cause only a small degree of bronchoconstriction prior to administration of immune complex cause a much stronger effect thereafter. Guineapigs (Dunkin-Hartley, male, 400–600g) are anaesthetised with phenobarbital (100 mg/kg i.p.) and pentobarbital (30 mg/kg i.p.) and paralysed with gallamine (10 mg/kg i.m.) and ventilated with a mixture of air and oxygen (45:55), v/v). Animals are ventilated (8 ml/kg, 1 Hz) via a tracheal cannula. Ventilation is monitored by a flow transducer. When making measurements of flow, coincident pressure changes in the thorax are monitored directly via an intrathoracic trochar, permitting display of differential pressure relative to the trachea. From this information resistance and compliance are calculated at each inspiration. An allergic reaction is initiated by intravenous injection of preformed immune complexes (prepared by adding 30 μg of bovine gamma globulin in 0.05 ml of saline to 0.05 ml of guinea pig anti-bovine gamma globulin anti-serum) 3 times at 10 minute intervals. Intravenous injections of histamine (1.0–3.2 μg/kg at 10 minute intervals) are used to define the sensitivity of the airways prior to and following the last exposure to the immune complex. Airways hyperreactivity is expressed as the paired difference for the maximal value of lung resistance in response to histamine before and after repeated injection of immune-complex. The agents of the invention are administered intratracheally either as solutions or suspensions in tragacanth. The $ED_{50}$. values for reversal of airways hyperreactivity are determined graphically from the dose response curves and represent those doses which cause a 50% reduction of airways hyperreactivity.

Diseases characterised by bronchial hyperresponsiveness to which the present invention is applicable include inflammatory or obstructive airways diseases, particularly asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or reduced airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

The agents of the invention may be administered by any appropriate route, e.g. orally, for example in the form of a tablet or capsule; parenterally, for example intravenously; topically, e.g. in an ointment or cream; transdermally, e.g. in a patch; by inhalation; or intranasally.

Pharmaceutical compositions containing agents of the invention may be prepared using conventional diluents or excipients and techniques known in the galenic art. Thus oral dosage forms may include tablets and capsules, and compositions for inhalation may comprise aerosol or other atomizable formulations or dry powder formulations.

The invention includes (A) an agent of the invention in inhalable form, e.g. in an aerosol or other atomizable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 1 μg to 10 mg/kg while for oral administration suitable daily doses are of the order of 0.1 mg to 1000 mg/kg.

A polypeptide (B) as hereinbefore described, or a mutant polypeptide as hereinbefore described associated with bronchial hyperresponsiveness, for example a polypeptide encoded by a variant of a polynucleotide comprising a nucleotide sequence encoding a polypeptide comprising amino acid sequence SEQ ID NO:7 or SEQ ID NO:8, which variant contains a sequence polymorphism, can be used to identify enhancers (agonists) or inhibitors (antagonists) of its activity, i.e. to identify compounds useful in the treatment of inflammatory or obstructive airways diseases, particularly asthma. The enhancers or inhibitors may be, for example, peptides, peptidomimetics, nucleic acids, or low molecular weight compounds. Accordingly, the invention also provides a method of identifying a substance which modulates the activity of a polypeptide (B) or a variant thereof associated with bronchial hyperesponsiveness, particularly a substance useful in the treatment of inflammatory or obstructive airways diseases such as asthma, comprising combining a candidate substance with said polypeptide (B) or said variant thereof and measuring the effect of the candidate substance on said activity. The activity of the polypeptide (B) or variant may be measured, for example, by promotion of homotypic $Ca^{2+}$ dependent aggregation and adhesion in L-cells e.g. as described by Sano et al, EMBO J. 12:2249–2256. The invention also includes a method of identifying a substance which binds to a polypeptide (B) or variant thereof as hereinbefore described, particularly a substance useful in the treatment of inflammatory or obstructive airways diseases such as asthma, comprising mixing a candidate substance with said polypeptide (B) or said variant and determining whether binding has occurred.

In another aspect the invention provides a method of identifying a substance which binds to, or modulates an activity of, a mutant polypeptide encoded by a variant of polynucleotide (A) as hereinbefore described, particularly a substance suitable for use in the treatment of an inflammatory or obstructive airways disease such as asthma, which comprises mixing a candidate substance with said mutant polypeptide and (i) determining whether binding has occurred and/or (ii) measuring the effect of the candidate substance on said activity.

The invention is illustrated by the following Examples. Abbreviations used in the Examples have the following meanings:

| | |
|---|---|
| AEBSF: | 4-(2-aminoethyl)benzenesulfonyl fluoride |
| BAC: | bacterial artificial chromosome |
| BAP: | 1,4-bis(acryloyl)piperazine |
| BHR: | bronchial hyperresponsiveness |
| BLAST: | basic local alignment search tool |
| BSA: | bovine serum albumin |
| CSGE: | conformation sensitive gel electrophoresis |
| dNTP: | deoxynucleotide triphosphate |
| DTT: | dithiothreitol |
| EIA: | enzyme immunoassay |
| EST: | expressed sequence tag |
| FAM: | 6-carboxy-fluorescein |
| FCS: | fetal calf serum |
| HBEC: | human bronchial epithelial cell |
| LBNL: | Lawrence Berkley National Laboratory |
| LOD: | logarithm of odds |
| MTN: | multiple tissue northern |
| ORF: | open reading frame |
| PAC: | P1 artificial chromosome |
| PCR: | polymerase chain reaction |
| PBS: | phosphate buffered saline |
| PEG: | polyethylene glycol |
| PMSF: | phenylmethylsulfonyl fluoride |
| SDS-PAGE: | sodium dodecyl sulfate polyacrylamide gel electrophoresis |
| SNP: | single nucleotide polymorphism |
| STS: | sequence tagged site |
| TAMRA: | 6-carboxy-tetramethyl-rhodamine |
| TDT: | transmission disequilibrium test |
| TET: | tetrachloro-6-carboxy-fluorescein |
| TTE: | 44 mM Tris, 14.5 mM taurine, 0.1 mM EDTA, pH 9.0 |

EXAMPLE 1

Asthmatic and non-asthmatic individuals are selected from a family study on the genetics of asthma in the Netherlands ([Panhuysen et al., Clin. Exp. Allergy 25 (suppl. 2): 35–38]; the Medical Ethics Committee of the University Hospital of Groningen and the University of Maryland approves this study and written informed consents are obtained from all participants). Between 1962 and 1975, patients with asthma are evaluated for diagnosis of asthma and optimization of their treatment in Beatrixoord, Haren, the Netherlands. For inclusion in this study, from this first evaluation patients have to meet three criteria: (1) symptoms consistent with asthma; (2) age≦45 years; (3) bronchial hyperresponsiveness to histamine ($PC_{20}$≦32 mg/ml using the de Vries 30 seconds inhalation method; [de Vries et al., Int. Arch. Allergy 20:93–101]). Clinical evaluation includes the performance of intracutaneous skin tests with common aeroallergens, pulmonary function testing with a water-seal spirometer (Lode Spirograph, Groningen, the Netherlands), and testing for bronchial hyperresponsiveness with histamine, using the 30 seconds inhalation protocol [de Vries et al., Int. Arch. Allergy 20:93–101]. Blood samples for DNA isolation and total IgE, specific IgE and eosinophil measurements are taken.

From 1990 onwards, these probands are re-studied together with their spouses, a minimum of two children and, if possible, grandchildren. In total, 200 two- and three generation families are studied. At this second evaluation (1990–1998), the measurements taken at the first evaluation (1962–1975) are repeated in the probands, and also performed in the relatives. Reversibility is tested by repeating spirometry 20 minutes after administration of 800 μg of salbutamol (albuterol). All participants are asked to stop pulmonary medication before the clinical testing if possible: inhaled corticosteroids are stopped for 14 days, inhaled long acting beta-mimetics and oral antihistamines 48 hours, inhaled short acting beta-mimetics and anticholinergics 8 hours. The asthma patients did not have an asthma exacerbation or require a course of oral prednisone in the 6 weeks prior to the study.

This evaluation further includes a modified version of the British Medical Council questionnaire with additional questions on symptoms and therapy of asthma and allergy [Panhuysen et al., Clin. Exp. Allergy 25 (suppl. 2): 35–38]. By definition, a physician's diagnosis of asthma is present in the probands. In the spouses, it is present if the subject reports (1) to be under current regular treatment for asthma, (2) has ever visited a general practitioner or specialist for asthma or (3) has ever used asthma medication. Allergic rhinitis is defined as a positive answer to one of the following questions: Do you have a runny or stuffed nose when you are in the surrounding of (1) animals (e.g. dogs, cats, horses), feathers (e.g. in pillows), or in a dusty part of the house?; or (2) trees, grasses, and flowers. Hay fever is defined as a positive answer to the question: have you ever had hay fever?

Serum total IgE is measured in the first 92 families by solid phase immunoassay [Panhuysen et al., Clin. Exp. Allergy 25 (suppl. 2): 35–38]. In the second set of 108 families, serum IgE levels are measured by an enzyme linked fluorescent assay (Mini Vidas, Biomerieux Vitek Inc., Marcy, France). Skin testing is performed by an intracutaneous skin test with 16 common aeroallergens, a positive, and negative control. The following allergens are tested: mixed grass pollens, two mixed tree pollens, mixed weeds, house dust mite, storage mite, cat-, dog-, horse-, rabbit/guinea pig dander, feather mix, and five moulds (*Aspergillus fumigatus, Alternaria alternata, Cladosporium herbarum, Penicillum notatum, Botrytis Cineria*). (ALK-Abelló, Nieuwegein, The Netherlands). A positive skin test is considered to be present if the largest wheal diameter is ≧5 mm.

Evidence for linkage of total serum IgE levels [Meyers et al., Genomics 23:464–470], bronchial hyperresponsiveness [Postma et al., New Eng J. Med. 333: 894–900] and asthma [Panhuysen et al., J. Invest. Med. 43: 281A; Bleecker et al., Am. J. Hum. Genet. 59:A213] to human chromosome 5q has previously been found in the Dutch families using a candidate gene approach. However, as has been found in other complex diseases, the region of linkage is wide (>40 cM spanning the region from the cytokine cluster to the $\beta_2$-adrenoceptor). In order to refine the region of linkage, DNA is extracted from blood DNA samples using standard protocols (Puregene kit, Gentra Systems Inc., Minneapolis, Minn.). A collection of 37 markers consisting of tri- and tetranucleotide repeats spanning the chromosome 5q31–q33 region is used to genotype the DNA samples. Multiplex PCR using fluorescently labelled primers is performed, and the resulting amplified fragments are separated on denaturing polyacrylamide gels. The labelled fragments are detected using the ABI377 sequencing machine and the genotypes scored using GENOTYPER software [Applied Biosystems, USA] using conventional techniques. A modified version of the program Linkage Designer [Van Camp et al., Trends Genet. 13:82] is used to bin alleles and to check inheritance. The output from Linkage Designer is then analysed for any inconsistencies using LINKAGE version 5.1 software [Lathrop and Lalouel, in *Handbook of Statistics*, Vol. 8., Rao and Chakraborty (eds), pp. 81–123. Elsevier Science Publishers BV, Amsterdam.] without disease information. As a final check of the data, CRIMAP [Lander and Green, Proc. Natl. Acad. Sci. USA 84:2363–2367] is used to determine the order and length of the chromosomal map and to detect double recombinants. In linked families, this analysis identifies a region of linkage for BHR with a LOD score in excess of 7.0: The peak LOD score is defined by microsatellite markers D5S2011 and D5S2017.

EXAMPLE 2

Bacterial artificial chromosome (BAC) clones spanning the chromosomal region between markers D5S2011 and D5S2017 identified using physical map information for human chromosome 5q31–q33 publicly available on the Lawrence Berkley National Laboratory Genome Centre web site (LBNL; www-hgc.lbl.gov/biology/bacmap/2.gif) obtained as BAC clone numbers h164 (22f14), c5 (50g20), h187 (35k5), h167 (8e5) and h177 (32d16) from Research Genetics (Huntsville, Ala., USA), and a P1 artificial chromosome (PAC) isolated by PCR using primers with SEQ ID NOS: 9 to 12 for the STS markers bac51107T (5' end of BAC 50g20) and bac51330T (3' end of BAC 22f14) available on the LBNL website ($www_{13}$ hgc.lbl.gov/sts.html) by Genome Systems Inc. (St. Louis, Mo., USA), the BACs and PAC together covering a sub-region of human chromosonal region 5q31–5q33, are sequenced using conventional techniques for an ABI 377 sequence. The resulting genomic DNA sequence is analysed using GENSCAN (Burge and Karlin, J. Mol. Biol. 268:78–94) and GENEMARK version 2.4 (Borodovsky and McIninch, Comp. Chem. 17:123–133) gene-finding programs and BLAST (Altschul et al., J. Mol. Biol. 215:403–410) homology searches against public protein, EST and DNA databases (SWISSPROT, SWISSPROTPLUS, GenBank, Genbank updates, EMBL, GENEMBLPLUS, GenBank EST, EMBL EST, GenBank STS, EMBL STS), the results of which are parsed into a human chromosome 5-specific version of ACeDb for graphic display. From this graphic display significant regions (i.e. genes) are identified by predicted exons and aligned EST/protein hits. A gene AAGA is initially identified on the graphic display as a GENSCAN-predicted gene covering at least 22.5 kb of genomic DNA and comprising 5 exons ranging in size from 153–2196 bp spread over two islands of DNA sequence separated by a stretch of unsequenced DNA:

| GENSCAN- | Nucleotide Position† In: | | Exon Size |
|---|---|---|---|
| Predicted Exon | SEQ ID No. 1 | SEQ ID No. 2 | (bp) |
| 1 | 1053–1889 | — | 837 |
| 2 | 5031–7226 | — | 2196 |
| 3 | 12987–13206 | — | 220 |
| 4 | 16002–16396 | — | 395 |
| 5 | — | 1695–1847 | 153 |

†the coordinates given are for the reverse complement of the original genomic sequence.

The DNA sequences in the GENSCAN-predicted exons encode a protein having homologies to cadherin-type molecules in a range of organisms, including humans, which suggest that it is a member of the cadherin protein family. A homology of 100% is detected with the mRNA sequences and ESTs corresponding to the protocadherin 42 gene (GENBANK accession numbers L11370, L11369 and AA481656). Alignment of the mRNA and EST sequences identifies three splice variants (SEQ ID Nos:4, 5 and 6), two of which have been previously identified (Sano et al., EMBO J. 12:2249–2256), and one (SEQ ID No:6) which is novel. Analysis of SEQ ID Nos:4, 5 and 6 for the longest open reading frame (ORF) using the EditSeq module of Lasergene software (DNASTAR, Inc., Madison, Wis., USA) reveals ORFs of 3198 nucleotides (SEQ ID No:4, position 377-3574) and 3729 nucleotides (SEQ ID Nos. 5 and 6, position 377-4105). It is noted that the ORF for SEQ ID No:4 is 118 nucleotides longer than that previously reported (position 494-3574; Sano et al., EMBO J. 12:2249–2256 and GenBank Accession No. L11370), translating to give a protein (SEQ ID No: 7) 39 amino acids longer than that predicted for GenBank Accession No. L11370 (1065 amino acids versus 1026 amino acids). The ORF for SEQ ID Nos:5 and 6 translates into a 1242 amino acid protein (SEQ ID No:8).

Using a 441 bp PCR fragment corresponding to exon 2 and generated from human genomic DNA using primers having SEQ ID NOS: 13 and 14, a northern blot of mRNA from a number of human tissues (human 12-lane MTN blot; Clontech Laboratories UK Ltd., Basingstoke, Hampshire, UK) is probed to examine the expression pattern of AAGA. Bands corresponding to the splice variants are detected in brain, heart, skeletal muscle, colon, kidney, liver, small intestine, pancreas and lung. No hybridisation is detected for thymus, spleen and peripheral blood lymphocytes. PCR analysis of first-strand cDNAs derived from various cell lines using primers having SEQ ID NOS: 13 and 14 shows that AAGA is expressed at a high level in activated and unactivated human bronchial epithelial cells (HBECs), at a medium level in fibroblasts, and at a low level in neutrophils and macrophages.

EXAMPLE 3

In this example conformation sensitive gel electrophoresis (CSGE: Ganguly et al., Proc. Natl. Acad. Sci. USA 90:10325–10329; Ganguly and Williams, Hum. Mut. 9:339–343) is used to detect potential sequence changes in PCR-amplified DNA fragments from blood DNA isolated from asthmatic patients. Single base mismatches in DNA heteroduplexes are detected by polyacrylamide gel electrophoresis in the presence of mildly denaturing solvents which amplify the tendency of mismatches to produce conformational changes and result in differential migration of homoduplexes and heteroduplexes. To generate heteroduplexes, amplified PCR products are thermally denatured, annealed, then analysed by polyacrylamide gel electrophoresis. DNA fragments are visualised by ethidium bromide staining. DNA fragments showing differential electrophoretic migration patterns are then sequenced to confirm the presence of a change to the polynucleotide sequence and the exact nature of this change.

SEQ ID NOs:4, 5 and 6 are manually aligned with SEQ ID NOs: 1 and 2 using the EditSeq module of Lasergene software (DNASTAR, Inc., Madison, Wis., USA). This analysis indicates that a 470 bp segment of DNA sequence at the 5'-end of SEQ ID Nos:4, 5 and 6 does not align with SEQ ID No:1 or 2. A BLAST search of the GENBANK database is undertaken using this 470 bp of mRNA sequence to identify the missing genomic sequence. This identifies a genomic DNA sequence of 2717 bp (SEQ ID NO:3) in GENBANK accession No. ACO13643 (154594 bp working draft sequence of 13 unordered pieces from human clone RP11–16P20). The alignment analysis reveals that the three alternative transcripts are derived from 7 exons spanning at least 21 kb of genomic DNA:

SPLICE VARIANT 1

| Exon | SEQ ID No. 4 | Nucleotide Position in SEQ ID No. 3† | Nucleotide Position in SEQ ID No. 1† | Exon Size (bp) |
|---|---|---|---|---|
| 1 | 1–456 | 2115–2570 | — | 456 |
| * | 457–470 | — | — | 14 |
| 2 | 471–1052 | — | 1030–1611 | 582 |
| 3 | 1053–1298 | — | 1648–1893 | 246 |
| 4 | 1299–4069 | — | 5035–7805 | 2771 |

SPLICE VARIANT 2

| Exon | SEQ ID No. 5 | Nucleotide Position in SEQ ID No. 3† | Nucleotide Position in SEQ ID No. 1† | Exon Size (bp) |
|---|---|---|---|---|
| 1 | 1–456 | 2115–2570 | — | 456 |
| * | 457–470 | — | — | 14 |
| 2 | 471–1052 | — | 1030–1611 | 582 |
| 3 | 1053–1298 | — | 1648–1893 | 246 |
| 4 | 1299–3490 | — | 5035–7226 | 2192 |
| 5 | 3491–3710 | — | 12987–13206 | 220 |
| 6 | 3711–4648 | — | 16002–16950 | 949 |

SPLICE VARIANT 3

| Exon | SEQ ID NO: 6 | Nucleotide Position in SEQ ID No. 3† | Nucleotide Position in SEQ ID No. 1† | Nucleotide Position in SEQ ID No. 2† | Exon Size (bp) |
|---|---|---|---|---|---|
| 1 | 1–456 | 2115–2570 | — | — | 456 |
| * | 457–470 | — | — | — | 14 |
| 2 | 471–1052 | — | 1030–1611 | — | 582 |
| 3 | 1053–1298 | — | 1648–1893 | — | 246 |
| 4 | 1299–3490 | — | 5035–7226 | — | 2192 |
| 5 | 3491–3710 | — | 12987–13206 | — | 220 |
| 6 | 3711–4591 | — | 16002–16896 | — | 895 |
| 7 | 4592–4684 | — | — | 797–889 | 93 |

*mRNA sequence does not align with genomic sequence available
†the coordinates given are for the reverse complement of the original genomic sequence.

PCR primer sets corresponding to AAGA gene sequence are designed using SEQ ID NOs:1 and 2 and Primer Express™ (version 1.0; Perkin Elmer, P/N 604313). These primer sets (SEQ ID NOs: 15–94) are:

| PRIMER SET | FORWARD | REVERSE |
|---|---|---|
| 1 | GTACACTACCCGAGTGGCGTG | CCTCTTACTGGCTCCTCCAGC |
| 2 | AGCTGGCCCCATACTCACC | CGTCCACTGGCTCTCTCTCC |
| 3 | TCCCGCCCATGGAACA | GACTTGGCATCTCAGAACAAAGAG |
| 4 | CTCCCCACATGCATGGTAGG | GCATGCTCTGGGGCATGT |
| 5 | TCCTCTTTTTCTGACAATCACCC | AAGGACAGGCCAGGGCAG |
| 6 | TTCTGGCAGTTTTTCCCCTAAG | GAGCTATTTGGGCTGCACGT |
| 7 | TCAAGCACGGTGACACGC | GCCCCCGGCTGCTAGA |
| 8 | TGGGACCAGCATCACGG | CAGCCGACTATGGTTTTCCAG |
| 9 | GATGCAGGGATCACCAGGG | CTTGCAGCCTTCCTGATTCTG |
| 10 | CTTGACACCAATGACAACGCC | TCAGAGGTTCCCCCAGCTT |
| 11 | TAGTGAGACCCCTTCTCCCCA | CTTTGTCAGGAAGAGGCAAAATG |
| 12 | AGGTGAGCTGAGTTGGAACAAAG | CCAAGCTGCCTAGTGCCTG |
| 13 | ATACATGCCTCCTCCCCTAGG | CACTTTGGCTTGAGGACCCA |
| 14 | CAGCCCCAGCTCCTTTCC | TGGGCCCGGTTTCTCAT |
| 15 | GGGGTACAATGGGCAGGTCT | AGTCTACTCCAAACCTAGGTCTCTATGTCA |
| 16 | TGGGACCCAGCCCCAG | GCACACGGATTAGGCTGAGTG |
| 17 | CCTACCACCCCCAACCCA | GAGCAGTACTCCGACTACAGCTACC |
| 18 | TGGCCCCCAACACGG | TCCCCGCATCCACCTG |
| 19 | AATGTGTTTGCAGGTGGCAG | GGAGGCCAAAAGTGGTTACCA |
| 20 | TCATCCTCGTCCTCCACTGG | GGCACAGCCTTGGTCCATC |
| 21 | TTGCCACGCTGCTTGGAG | GTCTTGGTGACACGGTCAGCC |
| 22 | GTGGCGCCGCTCAATCT | CAACGGTGACTTTGTTATCCAGAA |
| 23 | AAGCTGAGCGAGGTGGGA | GAGAGCTATGAGTTGAAGGTGGTG |
| 24 | CTGGCATGTTCTCCATCACTGAG | ACAACGCACCTGTCTTCACTCAG |
| 25 | AGATGGTGAAGAGGCCCTTAGC | GCAGGTGATGTGCCCTTCC |
| 26 | GGAGTTAGTGCTGGAGAGTGGG | CAAGAGTGCCCGTGCCC |
| 27 | GTCTCCTCTGCCACATCCTCTG | CCCTGATCTAAACCATCTCTGTTCTC |
| 28 | CTGTCCAGTCGAAGAAGACGC | TGTCCCATCTCCAATAGTTGCC |
| 29 | CAATACATAGATGATTTGTTTAAGGCCT | ATGGTGGTGGGCCCTGT |
| 30 | GACACTGCATGACCAGCAGG | ACTGGGCTCCTTCCCTTGAC |
| 31 | CCCTGCTTCAGGGCTAAAATT | CCAAATGGCCCATTCCAG |
| 32 | GATGGAAATGAGGGGAGAGGAC | ACACCAAAACGGCCCCC |
| 33 | GTGTGGCTGCGGGTGG | CCGCTCCCTCCTACAGACCT |
| 34 | CCGTTTTGGTGTTCCGGTC | TGCCTGTGAGTTCAGCGGT |
| 35 | ATCCCTGGCGCTGCG | CCCGATTAATACCAGTGCGG |
| 36 | TCCCAACCCAGGCATCC | AAAGGCGCTGTCCTCTCCA |
| 37 | CTTAGTTCTGGCCCCTGCCT | CTACAAACATTTCCTGAGCCCC |
| 38 | GCCAGAATTTCCGGCTCAA | CAACCCTTCCTAAACCTGAGGC |
| 39 | TCCTCACCCTTCACTGTGGG | CCTTGCTGCTTTCGGAGAGA |
| 40 | GGAGACCGAGGCTGAGACCT | AGCTGACGCGTTCTGAGGAT |

Using the above primer sets, 40 polynucleotides are amplified from blood DNA samples from 16 asthmatic patients. PCR reactions are carried out in a reaction volume of 10 µl containing 1× GeneAmpe® 10×PCR buffer (Perkin Elmer P/N N808-0240), 13 ng of template DNA, 400 µM of each dNTP (Amersham Life Science Nucleix Plus™ 25 mM dNTP mix; Prod. No. US77119), 30 ng of each primer, 2 mM MgCl$_2$ and 0.5 u of AmpliTaq Gold™ polymerase (Perkin-Elmer P/N N808-0242).

Typical thermal cycling conditions using a Biometra UNO II cycler (Part No. 050-603; Anachem Ltd., Luton, UK) are as follows, the sequence Step 2-Step 3-Step 4 being repeated 36 times:

| Step 1 | 95° C. | 10 min |
| Step 2 | 92° C. | 1 min |
| Step 3 | 60° C. | 1 min |
| Step 4 | 72° C. | 2 min |
| Step 5 | 72° C. | 10 min |

To generate heteroduplexes, 2 µl of PCR product is denatured at 95° C. for 10 minutes and annealed at 68° C. for 30 minutes using a thermal cycler (eg. Biometra UNOII). 2 µl of 2× loading buffer (20% ethylene glycol, 30% formamide, 0.025% xylene cyanol, 0.025% bromphenol blue) is added to each sample before gel analysis.

A standard DNA sequencing apparatus (Owl Scientific S3S; Autogen Bioclear UK Ltd.) is used with a 60 sample comb (Owl Scientific S2S-60A; Autogen Bioclear UK Ltd.) and standard power supply (Biorad, Cat No. 165-5057) equipped with a temperature probe (Biorad, Cat No. 165-5058). A 0.4 mm thick 15% polyacrylamide gel is prepared using a 99:1 ratio of acrylamide to BAP cross linker, 10% ethylene glycol and 15% formamide in 0.5×TTE. Gels are pre-run for one hour at 30 watts, limiting the temperature to a maximum of 25ûC (using an electric fan to keep the temperature down if necessary eg. Jencons, Cat No. 292-004). After the pre-run, the wells are flushed with a pipette and the samples are loaded into the wells. The gel is then electrophoresed at 12 watts overnight (15 hours) at 25° C. Fragments greater than 350 bp remain on the gel.

After electrophoresis, the gel plates are separated. The gel is stained by placing the gel in 0.5×TTE containing 1 µg/ml ethidium bromide (Biorad, Cat No. 161-0433) for 10 minutes, followed by destaining in 0.5×TTE for 10 minutes. The gel is then photographed on a UV transilluminator (eg. UVP GDS 7500).

Potential polynucleotide changes are detected by CSGE in one or more of the 16 patients for 15 of the 40 PCR fragments. For each of these potential changes, the POR fragment from all 16 patients is subjected to double stranded DNA sequencing on an ABI377 automated sequencer using standard methods and the resulting DNA sequence is analysed using CONSED software (Gordon et al., Genome Res. 8:195–202) to confirm the presence of a sequence change and to identify the exact base change. All of the 15 potential changes detected by CSGE are confirmed. The number of patients exhibiting the polymorphic changes are shown in the table below:

| Polymor-phism | SEQ ID No. 1 position | SEQ ID No. 2 (rev. comp.) position | SEQ ID No. 4 position | a.a. change | # patients |
|---|---|---|---|---|---|
| G to T | 589 | — | — | Intron 1 | 16 |
| C to T | 1001 | — | — | Intron 1 | 2 |
| C to A | 1060 | — | 501 | Pro3His (exon 2) | 16 |
| G to C | 2033 | — | — | Intron 3 | 1 |
| T to G | 2193 | — | — | Intron 3 | 1 |
| A to G | 2561 | — | — | Intron 3 | 16 |
| G to A | 5667 | — | 1931 | Ala480Thr (exon 4) | 1 |
| C to T | 5804 | — | 2068 | Pro525Pro (exon 4) | 1 |
| C to T | 6377 | — | 2641 | Ala716Ala (exon 4) | 14 |
| G to C | 7390 | — | 3654 | 3' untranslated | 5 |
| G to T | 7531 | — | 3795 | 3' untranslated | 1 |
| G to C | — | 1212 | — | 3' untranslated | 12 |
| G to A | — | 1216 | — | 3' untranslated | 1 |
| G to A | — | 1964 | — | 3' untranslated | 2 |
| G to A | — | 2330 | — | 3' untranslated | 5 |

Two of the detected polynucleotide changes alter the amino acid sequence (non-synonymous change) of the AAGA-encoded protein, 2 are synonymous (no residue change due to degeneracy of the genetic code), and 11 occur in non-coding regions of the gene.

Two hundred trios (both parents and an affected child) from the Dutch families are genotyped for SNPs at positions 1060, 2561, 6377, 7390 in SEQ ID NO:1 and position 2330 in SEQ ID NO: 2 by allelic discrimination assay using TaqMan™ technology on the ABI PRISM™ 7700 Sequence Detector (PE-Applied Biosystems, Warrington, UK). Two TaqMan™ fluorogenic probes, one specific to the non-SNP allele and one specific to the SNP allele, are designed to hybridise to the site of the SNP in the PCR-amplified target sequence:

| Position | SNP | | Non-SNP | |
|---|---|---|---|---|
| 1060 | TGCCTCAGGGGCTCCATCCT | (SEQ ID NO: 95) | TGTGCCTCAGGTGCTCCATCCT | (SEQ ID NO: 96) |
| 2561 | TGCCTCACCGGGCACACG | (SEQ ID NO: 97) | TGCCTCACCCGGCACACG | (SEQ ID NO: 98) |
| 6377 | TAGATCAGCTCGGCATTGACACCAG | (SEQ ID NO: 99) | CTGTAGATCAGCTCAGCATTGACACCAG | (SEQ ID NO: 100) |
| 7390 | CTCCCATGTGCCAGACCGGC | (SEQ ID NO: 101) | CCTCCCATGTACCAGACCGGCA | (SEQ ID NO: 102) |
| 2330 | TGCCCCAGGCACTAGGCAGCT | (SEQ ID NO: 103) | TGCCCCAGGCGCTAGGCA | (SEQ ID NO: 104) |

The TaqMan™ probes consist of an oligonucleotide with a fluorescent reporter dye (FAM or TET) and a quencher dye (TAMRA) covalently linked to the 5'- and 3'-ends, respectively. The proximity of the reporter dye to the quencher dye results in suppression of the reporter fluorescence in the intact probes. Upon amplification of the target sequence, the probe is cleaved during the extension step of the PCR. This removes the influence of the quencher dye and allows the reporter dye to fluoresce. As the SNP and non-SNP probes carry different reporter dyes, the level of fluorescence of each dye is proportional to the amount of SNP or non-SNP target sequence in the sample.

The transmission disequilibrium test [Spielman et al., Am. J. Hum. Genet. 52: 506–516] is used to test for a genetic association between the 5 genotyped SNPs and asthma/asthma subphenotypes. In this test an allele transmitted by a parent to an affected child is matched to the other allele not transmitted from the same parent; McNemar's chi-square test of discordance is then applied to the resulting pairs [Terwilliger and Ott, Hum. Hered. 42, 337–346]. TDT analysis of the genotype data obtained from the 200 Dutch asthma families reveals a strong genetic association between the SNPs at positions 6377 (p=0.00017) and 7390 (p=0.00049) in SEQ ID NO:1 and bronchial hyperresponsiveness and indicate that AAGA is a susceptibility gene for asthma and that individuals carrying the two SNPs are at increased risk for developing bronchial hyperresponsiveness. In addition, p=0.01 and p=0.001 are obtained for the SNPs at positions 6377 and 7390 respectively using the family based association test [FBAT; Horvath, Xu and Laird, Eur. J. Hum. Genet. 9, 301–306].

EXAMPLE 4

This Example relates to the expression of full length AAGA with a 6 histidine tag at the C-terminus using the Baculovirus system in T.m Hi5 cells, and to the purification of the resulting polypeptide.

1. Construction of a Recombinant AAGA Baculovirus

A unique EcoRI site is incorporated 5'to the AAGA start codon (position 377 in SEQ ID Nos: 4, 5 and 6) by PCR amplification using the following primer:

```
5ST
5'-GAAGATCTTCGGAATTCCATCATGGTGATGGGGAGCCCTTTGGAG-3' (SEQ ID NO: 105)
```

Another primer is used to introduce 6 histidine residues immediately prior to the AAGA stop codon (position 3574 in SEQ ID No:4 for 3ST1 and position 4105 in SEQ ID Nos:5 and 6 for 3ST2). This primer also incorporates a unique KpnI site 3' to the AAGA stop codon.

```
3ST1 (Splice variant 1)
5'-AAGATCTTCGGTACCTCAATGGTGATGGTGATGGTGCTCCCACACCTCGGTCCAG-3'   (SEQ ID NO: 106)

3ST2 (Splice variants 2 and 3)
5'-AAGATCTTCGGTACCTCAATGGTGATGGTGATGGTGCAGGTAGATCTCGCGCTTG-3'   (SEQ ID NO: 107)
```

The recombinant "His tagged" version of AAGA splice variant 1 is ligated as a 3208 bp EcoRI/KpnI fragment into EcoRI/KpnI digested pFastbac1 baculovirus transfer vector (Life Sciences). The recombinant "His tagged" version of AAGA splice variants 2 and 3 is ligated as a 3739 bp EcoRI/KpnI fragment into EcoRI/KpnI digested pFastbac1. The recombinant AAGA sequences are transposed into Bacmid DNA carried by DH10Bac cells (Life Sciences; Bac to Bac Baculovirus expression system). AAGA recombinant Bacmids are isolated from DH10Bac cells and transfected into Sf9 cells using published protocols (Bac to Bac baculovirus expression system manual; Life Sciences).

2. Amplification of Recombinant Baculovirus Stocks

The recombinant baculovirus is amplified by infecting Sf9 cells (maintained in SF900 SFMII medium; Life Sciences) at a cell density of $0.5 \times 10^6$ cells/ml and a multiplicity of infection (moi) of 0.01 for 96 hours. Sf9 cells are then centrifuged at 1000×g for 5 minutes. The supernatants containing high titre virus are stored at 4° C.

3. Expression of Recombinant AAGA in Hi5 Cells

Hi5 cells (Invitrogen), maintained at densities of between $3 \times 10^5$ and $3 \times 10^6$ cells/ml in Excell 401 medium (JRH Biosciences; distributed by AMS Biotechnology in either shaker flasks (rotated at 90 RPM) or spinner flasks (stirring at 75 RPM) are infected with the amplified recombinant Baculovirus at a cell density of $2.0 \times 10^6$ at an moi of 2.0 for 60 hours. Following infection Hi5 cells are centrifuged at 1000×g for 5 minutes, the supernatants poured off and the cell pellets frozen at −80° C.

4. Crude Lysate Preparation

The cells ($1 \times 10^9$) are resuspended in 100 ml lysis buffer (20 mM Hepes pH 7.5, 100 mM NaCl, 5% glycerol, 2 mM-mercaptoethanol, 0.5 mM imidazole, 0.1% Nonidet P-40, 40 µg/ml AEBSF, 0.5 µg/ml leupeptin, 1 µg/ml aprotinin and 0.7 µg/ml pepstatin A). Cells are incubated on ice for 15 min then centrifuged at 39,000×g for 30 min at 4° C. The sample is filtered through a 0.22 µm filter immediately prior to use.

5. Metal Chelate Affinity Chromatography

Metal chelate affinity chromatography is carried out at room temperature with a column attached to a BioCAD chromatography workstation. A 20 ml Poros MC/M (16 mmD×100 mmL) column is charged with $Ni^{2+}$ prior to use and after each purification. To charge with $Ni^{2+}$, the column is washed with 10 column volumes (CV) 50 mM EDTA pH 8, 1 M NaCl followed by 10 CV water. The column is charged with 500 ml 0.1 M NiS04 pH 4.5–5, washed with 10 CV water, then any unbound $Ni^{2+}$ removed by washing with 5 CV 0.3 M NaCl. All steps are performed with a flow rate of 20 ml/min. The charged MC/M column is saturated with 5 CV Buffer B (20 mM Hepes pH 7.5, 500 mM NaCl, 5% glycerol, 2 mM β-mercaptoethanol, 1 mM PMSF, 250 mM imidazole) followed by equilibration with 10 CV Buffer A (as Buffer B except 0.5 mM imidazole). 90–95 ml of the crude lysate is loaded onto the column per run at a flow rate of 20 ml/min. Subsequent steps are carried out with a flow rate of 30 ml/min. Any unbound material is removed by washing with 12 CV buffer A and AAGA eluted by applying a 0–100% Buffer B gradient over 10 CV. Fractions (8 ml) are collected over the gradient. AAGA-containing fractions are combined and protease inhibitors added to the final concentrations described for the lysis buffer above. DTT is also added to a final concentration of 1 mM. The combined fractions are dialysed overnight against 4 liters 20 mM Tris-HCl pH 7.5, 1 mM DTT, 0.2 mM PMSF at 4° C.

6. Ion Echange (Anion Exchange) Chromatography

Resource™ Q chromatography is carried out at 4° C. with a column attached to an FPLC workstation (Amersham Pharmacia Biotech). A 6 ml Resource™ Q column (16 mmD×30 mmL) is equilibrated with 10 CV Buffer C (20 mM Tris-HCl pH 7.5, 1 mM DTT) at a flow rate of 2 ml/min. The dialysed metal chelate eluate is applied to the column and washed with 10 CV Buffer C. The protein is eluted by applying a 0–100% Buffer D gradient (20 mM Tris-mM HCl pH 7.5, 1 mM DTT, 1 M NaCl) over 10 CV. Fractions (3 ml) are collected on eluting the column.

7. Gel Filtration

Gel Filtration chromatography is carried out at 4° C. with a column attached to a BioCAD SPRINT chromatography workstation (PE Biosystems). A 24 ml (10 mmD×300 mmL) Superdex 200 HR (Amersham Pharmacia Biotech) column is equilibrated with 10 CV Buffer E (20 mM Tris-HCl pH 7.5, 1 mM DTT, 150 mM NaCl) at a flow rate of 0.5 ml/min. The ion exchange eluate is applied to the column and eluted with Buffer E. Fractions (1 ml) throughout the purification run are collected and analysed.

8. Sample Concentration

Samples are concentrated approximately 10-fold using a Millipore Ultrafree-15 centrifugation device (MW cut-off 50 kDa) at 4° C. The device is pre-rinsed with water prior to use. The final storage buffer used for long term storage at −80° C. is 20 mM Hepes pH 7.5, 1 mM DTT, 100 mM NaCl, 5% glycerol. Glycerol can be omitted from the sample for storage at 4° C.

EXAMPLE 5

This example relates to the production of polyclonal antibodies against AAGA protein purified as described in Example 4.

Immunisation of Rabbits:

Dutch rabbits (Harlen-Olac) are immunised at 4 subcutaneous sites with 500 µg purified AAGA protein in PBS according to the following schedule:

| DAYS | IMMUNISATIONS |
| --- | --- |
| 0 | 1st immunisation 1:1 in complete Freund's adjuvant |
| 15 | 1st boost 1:1 in incomplete Freund's adjuvant |
| 45 | 2nd boost 1:1 in incomplete Freund's adjuvant |
| 55 | 1st test bleed from the ear artery |
| Every month | Boost 1:1 in incomplete Freund's adjuvant until a good antibody response is obtained |

Test bleeds (500 µl) are taken and the serum assessed for antibody titre. Serum is collected when a maximum titre is reached. This is done by collecting blood (10 ml) and allowing it to clot for 2 hours at 4° C. The blood is centrifuged at 1000×g for 5 minutes to separate the serum. The serum is removed and stored at −20° C. until assayed.

ELISA Screening:

Nunc-Immuno Plate Maxisorp 96 well plates (Nunc, Fisher Scientific UK, Loughborough, UK) are used as a solid support and coated with the purified AAGA protein (100 ng/well) overnight at 4° C. The plates are blocked for 3 hours at 37° C. with PBS containing 2% BSA (Sigma) and 0.02% NaN$_3$ (Sigma). After blocking, plates are incubated overnight at room temperature with serum in different dilutions of PBS. The presence of polyclonal antibodies is checked with both biotin labelled IgG-antibodies to rabbit (Goat anti-rabbit IgG antiserum, 1:25000 dilution), with an incubation time of 40 min. Alkaline phosphatase conjugated streptavidin (Immununo Research, Dianova, CH) is then added at a dilution of 1:10000. Development of the reaction is carried out by adding an alkaline phosphatase substrate (Sigma, f.c. 1 mg/ml) dissolved in diethanolamine. After 45 min. absorbance is read at 405 nm with a reference of 490 nm with an ELISA plate reader (Bio-rad laboratories Ltd., Hemel Hempstead, UK).

Purification:

5 ml protein A-agarose is poured into a chromatography column and washed with 6 column volumes of 0.1 M tris (hydroxymethyl) methylamine (Tris) buffer pH 7.5. The rabbit serum containing anti-AAGA antibodies is diluted (1/2) with Tris buffer and added to the protein A-agarose. Unbound proteins are removed by washing the column with 6 volumes of Tris buffer. The IgG is eluted off the column with three column volumes of 0.1 M glycine buffer pH 3.0 and collected as 1 ml fractions into tubes containing 28 µl of 1 M Tris. The fractions which are positive for protein content are checked for purity by SDS-PAGE under reducing conditions. Two bands at 50 and 25 Kd are visualised corresponding to the heavy and light chains of an immunoglobulin molecule. Fractions containing only immunoglobulin are pooled, re-checked for protein concentration and stored at −20° C.

EXAMPLE 6

This example describes the preparation of monoclonal antibodies against AAGA protein purified as described in Example 4.

Immunisation of Mice:

Female Balb/c mice are immunised intraperitoneally with 100 µg of AAGA protein in PBS according to the schedule given below:

| DAYS | IMMUNISATIONS |
| --- | --- |
| 1 | 1st immunisation 1:1 with complete Freund's adjuvant |
| 14 | 1st boost 1:1 with incomplete Freund's adjuvant |
| 21 | 2nd boost 1:1 with incomplete Freund's adjuvant |
| 28–30 | Three final boosts in PBS |
| 31 | Fusion with mouse myeloma cells |

Serum is assessed for anitbody titre by ELISA (Example 5) after the animal is sacrificed for the preparation of spleen cells for fusion. If antibody titre is sufficient, (1/1000 to 1/100,000), the hybridomas are screened otherwise discarded.

Preparation of Myeloma Cells

Sp2/0 murine cells (ATCC #CRL 1581; maintained in culture medium containing 20 µg/ml 8-azaguanine) are cultivated for one week before fusion in RPMI 1640 (8-azaguanine is not included), 10% (v/v) FCS and 1% penicillin-streptomycin (50IU/ml and 50 µg/ml, respectively). The cells are harvested by centrifugation (200×g for 5 min) and washed three times in cold RPMI 1640. Approximately 2.5×10$^6$ cells are used per 96 well microtitre plate.

Preparation of Spleen Cell Suspension

The mouse is killed by an overdose of anesthetic (Forene), the spleen dissected and pressed through a cell strainer (70 µm mesh cell strainer; Becton & Dickinson, Oxford, UK, Cat. No 2350). The cell suspension is washed three times in RPMI 1640 (as above) and counted: $5.10^6$ cells/96 well plate are necessary.

Fusion of Myeloma Cells and Spleen Cells

The spleen and myeloma cells are mixed (2:1), centrifuged (200×g for 5 min) and the pellet warmed in a 37° C. water bath. Prewarmed polyethylene glycol 4000 (1 ml per $10^8$ cells) is added slowly over one minute, then 20 ml of prewarmed wash medium over two minutes. After centrifugation the pellet is carefully resuspended in selection medium (RPMI 1640, 10% FCS, 1% penicillin-streptomycin, 10% BM condimed H1 (feeder cell replacement from Boehringer Mannheim, Lewes, UK; Cat. No. 1 088 947), 10% HAT-media supplement (hypoxanthine, aminopterin and thymidine to select against unfused myeloma cells; Boehringer Mannheim, Lewes, UK; Cat. No. 644 579) and plated, 200 µl/well of a 96 well microtitre plate. After five days clusters of hybrid cells can be identified by examining the bottom of the microtitre wells with an inverted microscope. After 10–14 days the culture supernatant is tested for the presence of antibodies by ELISA (example 4). The positive clones are expanded in a 24 well assay plate and retested.

Cloning of Positive Hybridomas

The expanded clones which are still positive are cloned by limiting dilution. Cells are diluted serially in four dilutions steps in a 96 well microtitre plate; 5, 2, 1 and 0.5 cells/well. HAT-media supplement is replaced with HT-media supplement (Boehringer Mannheim, Lewes, UK; Cat. No. 623 091). After approximately one week the cells are screened by ELISA (Example 4). The cells of those wells containing a single positive clone are expanded.

Production of Monoclonal Antibody Supernatant

The cells are grown in culture flasks in standard medium (RPMI 1640, 10% (v/v) FCS and 1% penicillin-streptomycin) until the hybridomas overgrow and die. The debris is removed by centrifugation and the supernatant containing the antibodies is titred using ELISA (Example 4) before storing under sterile conditions at 4° C., –20° C. or –70° C.

What is claimed is:

1. A method for determining whether a subject has, or is at risk of developing asthma characterized by bronchial hyperresponsiveness, comprising determining, in a sample of cells from the subject the presence of a variant of a polynucleotide (A) comprising the nucleotide sequence of SEQ ID NO: 1 associated with asthma characterized by bronchial hyperresponsiveness, said variant of polynucleotide (A) having a T at position 6377 in SEQ ID NO: 1 and/or a C at position 7390 in SEQ ID NO: 1 and determining that said subject has or is at risk of developing asthma characterized by bronchial hyperresponsiveness if said variant is present.

2. A method according to claim 1, in which the variant of polynucleotide (A) comprises either a T at position 6377 of SEQ ID NO: 1 or a C at position 7390 of SEQ ID NO: 1 and the variant is identified by sequencing a DNA sample from the subject.

3. A method according to claim 2, in which the variant has a T at position 6377 in SEQ ID NO: 1.

4. A method according to claim 1, in which determining the presence of a variant of a polynucleotide (A) comprises determining, in a sample of cells from a subject, the identity of T at position 6377 in SEQ ID NO:1.

* * * * *